US011095587B2

(12) United States Patent
Ichikawa et al.

(10) Patent No.: US 11,095,587 B2
(45) Date of Patent: Aug. 17, 2021

(54) TECHNIQUES FOR HANDLING MESSAGES IN LABORATORY INFORMATICS

(71) Applicant: WATERS TECHNOLOGIES IRELAND LIMITED, Dublin (IE)

(72) Inventors: Yoji Ichikawa, Milford, MA (US); Cynthia Miller, Milford, MA (US); James Busker, Milford, MA (US); Puneet Rachhoya, Milford, MA (US); Xiao Run Jin, Milford, MA (US); Azmy Sukkoor, Milford, MA (US)

(73) Assignee: WATERS TECHNOLOGIES IRELAND LIMITED, Dublin (IE)

( * ) Notice: Subject to any disclaimer, the term of this patent is extended or adjusted under 35 U.S.C. 154(b) by 0 days.

(21) Appl. No.: 16/436,684

(22) Filed: Jun. 10, 2019

(65) Prior Publication Data

US 2019/0379621 A1 Dec. 12, 2019

Related U.S. Application Data

(60) Provisional application No. 62/682,595, filed on Jun. 8, 2018.

(51) Int. Cl.
*H04L 12/58* (2006.01)
*G06Q 10/10* (2012.01)
(Continued)

(52) U.S. Cl.
CPC ............ *H04L 51/12* (2013.01); *G06Q 10/107* (2013.01); *H04L 51/02* (2013.01); *G06F 16/951* (2019.01); *G06F 16/953* (2019.01)

(58) Field of Classification Search
CPC ....... H04L 51/12; H04L 51/02; G06Q 10/107; G06F 16/951; G06F 16/953; G16H 10/40; G16H 40/40
See application file for complete search history.

(56) References Cited

U.S. PATENT DOCUMENTS 9,235,641 B1   1/2016 Kumar
2005/0060191 A1* 3/2005 Parkins ................. G06Q 50/24
                                                         705/2

(Continued)

FOREIGN PATENT DOCUMENTS

JP    H11122276 A    4/1999
WO    2004027677 A1   4/2004

OTHER PUBLICATIONS

International Search Report and Written Opinion for International application No. PCT/US2019/036401, dated Aug. 29, 2019, 14 pages.

*Primary Examiner* — Philip J Chea
*Assistant Examiner* — Wuji Chen
(74) *Attorney, Agent, or Firm* — Kacvinsky Daisak Bluni PLLC

(57) ABSTRACT

Various embodiments may be generally directed to techniques for handling messages in laboratory informatics, such as managing and viewing messages associated with a project that utilizes multiple laboratory data devices and/or applications, for instance. In many embodiments, managing the messages may include storage and retrieval of messages, creating and maintaining audit trails, as well as providing alerts based on the messages. In several embodiments, viewing the messages may include filtering and searching messages. Some embodiments may be particularly directed to managing and viewing messages associated with data devices used in conjunction with liquid chromatography and/or mass spectrometry.

16 Claims, 30 Drawing Sheets

(51) Int. Cl.
   *G06F 16/953* (2019.01)
   *G06F 16/951* (2019.01)

(56) References Cited

U.S. PATENT DOCUMENTS

| | | | | |
|---|---|---|---|---|
| 2006/0020398 A1* | 1/2006 | Vernon | ............... | G16B 25/00 702/20 |
| 2007/0250274 A1* | 10/2007 | Volkov | ............... | C12Q 1/6813 702/22 |
| 2011/0313790 A1* | 12/2011 | Yao | ............... | G06Q 50/22 705/3 |
| 2011/0314148 A1 | 12/2011 | Petersen et al. | | |
| 2014/0032694 A1* | 1/2014 | Cohn | ............... | G06F 11/3072 709/207 |
| 2015/0198573 A1* | 7/2015 | Habel | ............... | G01N 30/86 702/50 |

\* cited by examiner

Storage Medium 1400

*Computer Executable Instructions*

TECHNIQUES FOR HANDLING MESSAGES IN LABORATORY INFORMATICS

CROSS-REFERENCE TO RELATED APPLICATION

This application claims the benefit of U.S. Provisional Patent Application No. 62/682,595, filed on Jun. 8, 2018, the entire disclosure of which is incorporated by reference.

BACKGROUND

Chromatography and spectrometry may include the separation and/or identification of different constituents of a mixture or sample. Informatics may include aspects of processing data for storage and retrieval. The performance of chromatography or spectrometry procedures may generate data or messages regarding one or more aspects of the chromatography or spectrometry procedures.

SUMMARY

Various embodiments may be generally directed to techniques for handling messages in laboratory informatics, such as managing and viewing messages associated with a project that utilizes multiple laboratory data devices and/or applications, for instance. In many embodiments, managing the messages may include storage and retrieval of messages, creating and maintaining audit trails, as well as providing alerts based on the messages. In several embodiments, viewing the messages may include filtering and searching messages. Some embodiments may be particularly directed to managing and viewing messages associated with data devices used in conjunction with liquid chromatography and/or mass spectrometry. These and other embodiments may be described and claimed.

Some challenges facing laboratory informatics may include the inability to manage and view messages associated with or generated by data devices and/or applications in an efficient manner. Such messages may include information regarding an error or fault condition detected in a laboratory device (e.g., in a liquid chromatography or mass spectrometry device), information regarding the initiation or completion of a particular test sequence or calibration sequence, or an error or fault condition detected with the results obtained by a laboratory device (either for a sequence in process or a sequence that has completed). For instance, maintaining accessibility to messages in an online environment may require excessive memory, leading to slow and inefficient interfaces and poor user experiences. In various embodiments, messages may not be maintained in a way that meets regulatory standards. For instance, linkages between audit trail records and messages may not be established. Additionally, messages may have varying levels of importance and require manual and time-consuming filtering and/or searching to identify urgent and/or relevant messages. These and other factors may result in message controllers with limited flexibility, low efficiency, and/or deficient performance. Such limitations may drastically reduce the capabilities, usability, and applicability of message controllers in conjunction with laboratory informatics, contributing to ineffective systems with limited applicability.

Various embodiments described herein include a message controller that provides efficient and intuitive message viewing and message management. In some embodiments, the message controller may reduce a number of online messages by archiving messages offline in a manner that allows the offline messages to still be readily accessed, viewed, and/or searched. For instance, messages may be archived in dump files that may still be tracked and/or searched. In various embodiments, the message controller may maintain messages in a manner that meets regulatory standards. For example, linkages between audit trail records and messages may be established and maintained. In these and other ways one or more of the message controllers described herein may provide message management and/or viewing in an accurate, reliable, adaptable, and efficient manner to achieve improved message controllers in conjunction with laboratory informatics, resulting in several technical effects and advantages.

BRIEF DESCRIPTION OF THE DRAWINGS

FIGS. 4A and 4B illustrate exemplary aspects of a message center according to one or more embodiments described herein.

FIGS. 5A-5D illustrate exemplary aspects of a view filter editor according to one or more embodiments described herein.

FIGS. 12A-12C illustrate exemplary aspects of table space usage according to one or more embodiments described herein.

FIG. 14 illustrates an embodiment of a storage medium according to one or more embodiments described herein.

DETAILED DESCRIPTION

Figure 1:
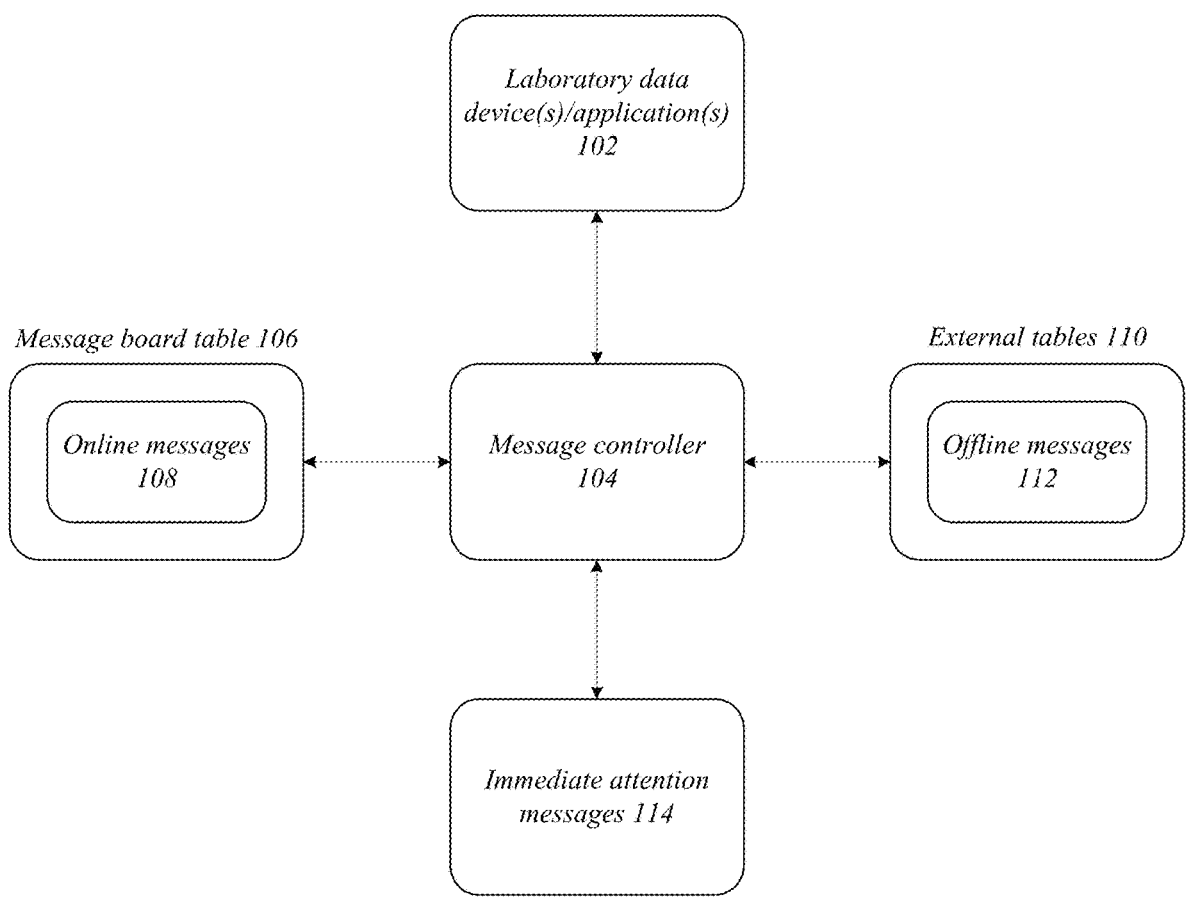
FIG. 1 illustrates an example of a message handling system according to one or more embodiments described herein.

Reference may be now made to the drawings, wherein like reference numerals may be used to refer to like elements throughout. In the following description, for purpose of explanation, numerous specific details may be set forth in order to provide a thorough understanding thereof. It may be evident, however, that the novel embodiments may be practiced without these specific details. In other instances, well known structures and devices may be shown in block diagram form in order to facilitate a description thereof. The intention may be to cover all modification, equivalents, and alternatives within the scope of the claims.

FIG. 1 illustrates an embodiment of an operating environment 100 that may be representative of various embodiments of a message handling system. Operating environment 100 may include laboratory data device(s)/application (s) 102, message controller 104, message board table 106 with online messages 108, external tables 110 with offline messages 112, and immediate attention messages 114. In various embodiments described herein, messages controller 104 may receive data from one or more laboratory data device(s)/applications 102 and generate one or more online messages 108 in the message board table 106, one or more offline messages 112 in one or more external tables 108 and/or one or more immediate attention messages 114 based on the application of rules/preferences. In many embodiments, the rules/preferences may generate audit trail records to meet regulatory requirements associated with curating the messages. For instance, a block chain associated with one or more messages may be automatically generated by the message controller 104. Embodiments are not limited in this context.

In some embodiments, online messages 108 in message board table 106 may include the most recent messages that a user needs to be aware of (e.g., a just in time (JIT) view). In some such embodiments, the online messages 108 may reside in the message board table 106, also referred to as the online table. In various embodiments, offline messages 112 may include messages archived in one or more external tables 110 that may be no longer necessary to actively show in the online table. In some embodiments, external tables 110 may be referred to as offline tables and/or offline messages 112 may be referred to as nearline messages or archived messages. In one or more embodiments, message controller 104 may be able to archive or backup online messages 108 as offline messages 112, such as by moving online messages 108 to a dump file.

In many embodiments, message controller 104 may provide or serve one or more of the following functions associated with messages including a graphical user interface (GUI), paging, message tracking, searching, archiving, prioritizing, alerting, filtering, error notifications, block chain, auditing, regulatory, and the like. In several embodiments, message controller 104 may be able to display both online messages 108 and offline messages 110 in a single table. In several such embodiments, displaying online messages 108 and offline messages 110 in a single table may enable intuitive searching of messages. In some embodiments, message controller 104 may create, maintain, and/or update a message tracking information entry table to record information about each message that has been exported from the message board table 106 to one or more external tables 110. In some such embodiments, the message tracking information entry table may enable one or more of searching, indexing, reviewing, and auditing offline messages 112.

In one or more embodiments, immediate attention messages 114 may include one or more emails, phone calls, or text messages sent to a defined address in response to a message received from one or more of laboratory data device(s)/application(s) 102. For instance, messages that meet certain requirements, such as a high enough priority level, may cause message controller 104 to generate and send a text message to the mobile phone of one or more users, such as a project lead or administrator. In various embodiments, the requirements to send immediate attention messages 114 may be customized based on preferences and/or a type of project being performed/monitored by laboratory data device(s)/application(s) 102. In some embodiments, immediate attention messages 114 may be stored with one or more of the online messages 108 and offline messages 112. Various aspects of message controller 104, message board table 106, online messages 108, external tables 110, offline messages 112, and/or immediate attention messages 114 may be described in more detail below, such as in conjunction with one or more of FIGS. 3-16.

Figure 2:
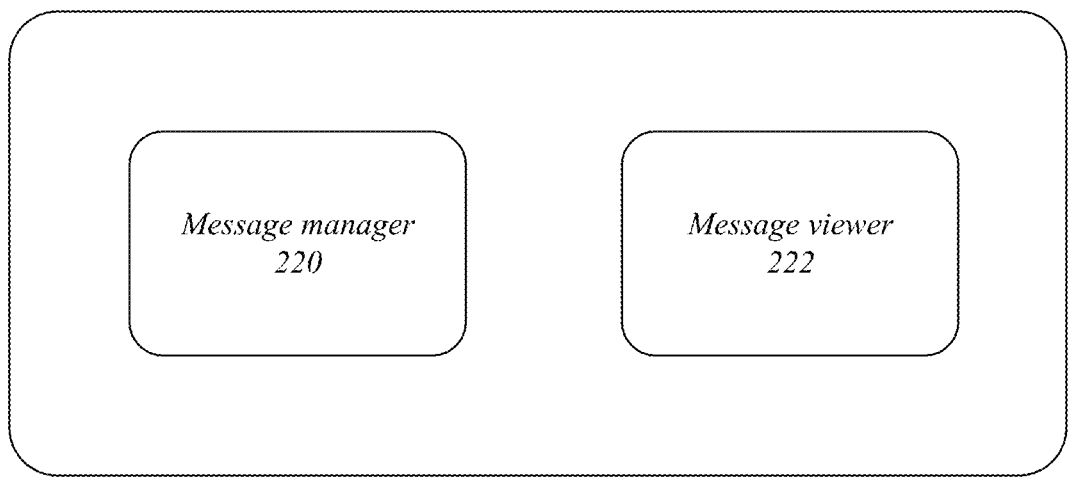
FIG. 2 illustrates an example of a message controller according to one or more embodiments described herein.

FIG. 2 illustrates an embodiment of an operating environment 200 that may be representative of various embodiments. Operating environment 200 may include message controller 104 with a message viewer 212 and a message manager 214. In one or more embodiments described herein, message manager 220 may be responsible for storing and tracking messages while message viewer 222 may be responsible for providing access to messages. Various aspects of message manager 220 and/or message viewer 222 may be described in more detail below, such as in conjunction with one or more of FIGS. 3-16. Embodiments are not limited in this context.

Figure 3:
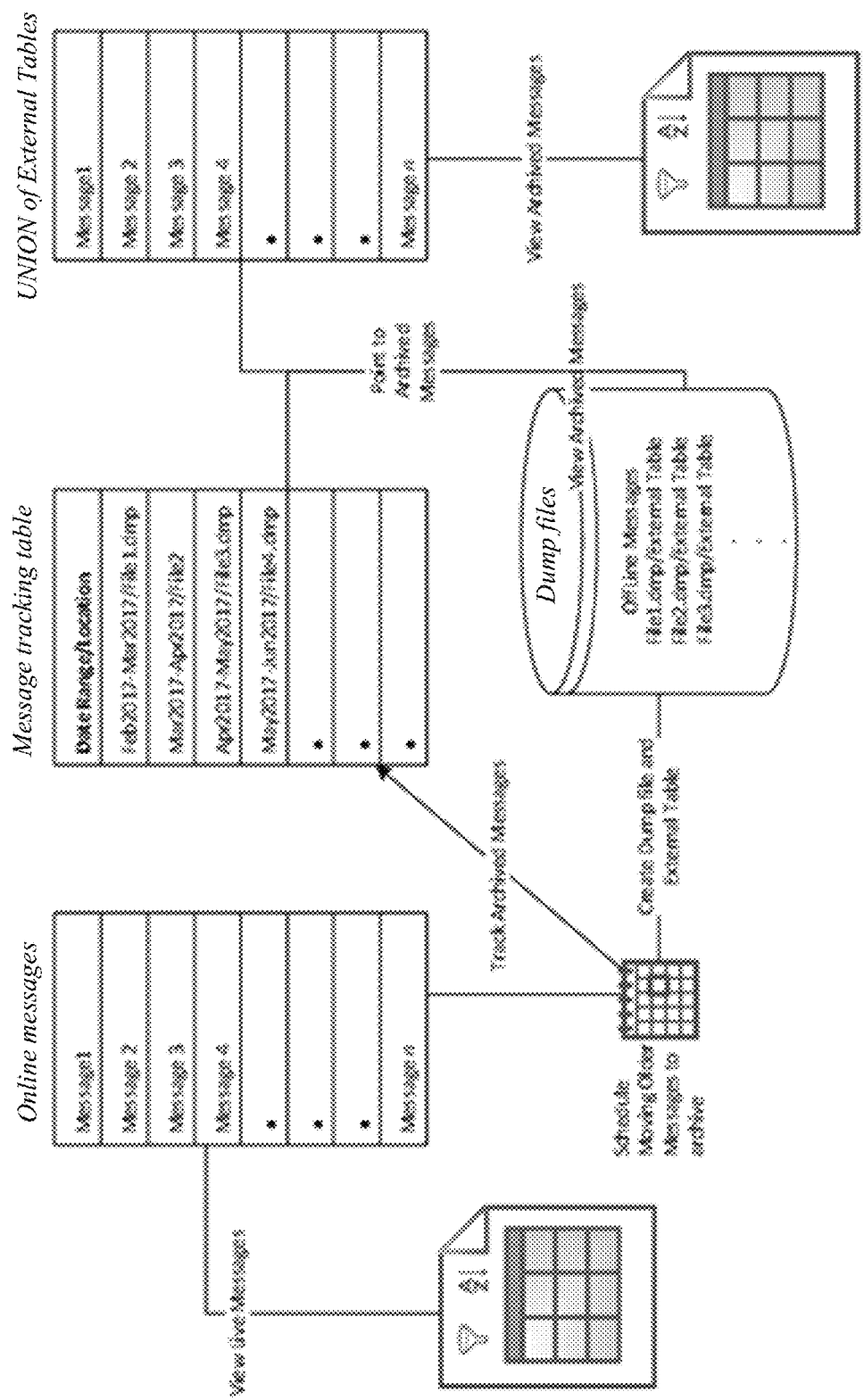
FIG. 3 illustrates an example of a message lifecycle according to one or more embodiments described herein.

FIG. 3 illustrates an example of a message lifecycle according to one or more embodiments described herein. In various embodiments, the message lifecycle may illustrate various functional aspects and/or capabilities of message controller 104. In some embodiments, different components of message controller 104 may be responsible for different aspects of the message lifecycle. For instance, message manager 220 may be responsible for archiving or tracking messages while message viewer 222 may be responsible for retrieving, viewing, or filtering messages. Embodiments are not limited in this context.

In some embodiments, external tables may allow for normal queries. In many embodiments, external tables may be read only. In several embodiments, the external tables may live in a file, such as a dump file (e.g., File1.dmp/External Table). In one or more embodiments, individual external tables may be constructed as messages may be archived. Various embodiments, may ensure that data base backups backup the external table files. In some embodiments external files may need to be considered in restore database documentation. In one or more embodiments, users may select the messages to be archived by data range.

In one or more embodiments a message sequence may be used to ensure that all message may be present (no gaps). In one or more such embodiments, other tables may be prevented from using the sequence. For instance, when messages may be throttled such as repeat instrument messages that do not use a sequence until it may be determined the message may be kept. In many embodiments, a just in time (JIT) message view, such as one implemented by message viewer 222, may provide an advantageous and novel way to view the most recent messages (e.g., the live messages).

In some embodiments an enable large addresses flag may be used to allow message controller 104 and/or laboratory data device(s)/application(s) 102 to may have access to more memory. For instance, the enable large address flag may allow an application to use up to 4 GB of memory versus the 2 GB without the flag.

In various embodiments, different privileges and/or trust levels may be allotted to different users. For instance, access to certain components or features, such as access to numerical and/or textural results, may be restricted via a review privilege. In some embodiments the privileges may be set in User Type properties in Management tab. In many embodiments, privileges may be enabled by default for all default user types and all new user type. A user without the review privilege may not be able to see one or more of Result Window, Calibration Curve Window, Mass Analysis Window, Result Audit Viewer, Peak Table, Spectrum Index Tab, the content of the 3D Layout, the Results field in Legend tab and Peak labels. The privilege may also be added in a toolkit.

In various embodiments project integrity tests may be performed prior to running backup. This project integrity test may involve the following processes: (1) check to see if all channels in the project may have raw data file associated, if any channels do not may have a raw data file, the integrity test fails; and (2) check all raw data files for errors of checksum file, data incomplete, and acquisition in progress, if any checksums are not correct, the data may be incomplete, or acquisition may be in process, the integrity test fails.

In many embodiments, a user may run an integrity test on a project and/or its sub-projects when the following conditions are met: (1) the user has access to the project and (2) the project may be not part of another operation that restricts access to it (archiving, moving the raw data files from one Raw data share location to another or deleting the project). In some embodiments, if the project is part of a hierarchy and integrity test is triggered from the root project the user should have access to the entire hierarchy chain, otherwise whenever a project without access is encountered a warning message may popup stating that neither the project to which the user doesn't have access to, or its sub projects, may be analyzed.

In some embodiments, a "Test Project Integrity" button may be created on the Integrity tab of the Project Properties dialog. When the user clicks on the button, the button may be disabled until the process may be finished, and the result may be added in the table. Only the selected project may be tested (if this project has child projects, they may be not tested). While the integrity test may be in process, the OK and Cancel buttons may be grayed out but the Help and Details buttons may be available. The OK and Cancel buttons become active after the integrity test may be completed.

In several embodiments, a "Test Project Integrity" menu item may be also added to Configuration Manager. In Configuration Manager right clicking on one or more selected projects in the Project window or on a single project in the project tree there may be a menu item to Test Project Integrity.

In many embodiments, when the integrity test function may be triggered by right clicking on one or more projects in configuration manager (either in the tree or in the table) the application may check if the selected proj ect(s) may have child projects. If they do, the user may be asked if they want to perform an integrity test on the sub-projects as well or cancel the integrity test. If the answer may be yes and the user has access to them, the child projects may be also tested. If the answer may be no, only the selected parent project(s) may be tested. If cancel may be selected, no project integrity testing may be done.

Whenever the integrity test may be triggered one or more of the following things may happen: (1) An entry may be made to the System Audit Trail indicating whether the integrity test succeeded or failed. The entry may reference the project in which the integrity test was run. (2) For each project whose integrity may be tested (parent and possibly child project(s)) a new entry in the configuration manager project property integrity tab table may be made which contains the report of the integrity test analysis. (3) While testing integrity of a single project, if the integrity test fails the user may be prompted that errors may have been found and an entry type "error" may be added to the message center stating that one or more project integrity errors were detected in the project. While testing integrity of multiple projects and integrity fails on one or more projects, no pop up message may be displayed and appropriate messages may be sent to the message center for each failed project. (4) Whenever integrity may be tested on multiple projects, a batch integrity timestamp log file may be created and stored in the \Logs directory indicating whether the integrity test for each project in the batch succeeded or failed. (5) If the project may be in the process of being moved or deleted a warning message may pop up and that project may not be tested. If testing integrity on multiple projects, this pop up may be seen for each project that may be being moved or deleted. (6) A project integrity test may be allowed while data may be being acquired into that project and while data may be being processed in that project.

In some embodiments, attempting to run an integrity test on a project that has been deleted, may cause the integrity test to be cancelled and a message may be displayed like the following: "Testing project integrity has been cancelled on all selected projects because project <projectname> has been deleted. The Projects View may be updated automatically so that the project integrity test can be repeated."

In order to implement these enhancements a table may be added to a database to provide a place to store MessageTrackingInfo. This table may have a row for each external table created when messages may be moved from the online (Message Board) table to a nearline messages table that may be implemented as a data structure, such as a table (for instance, an Oracle® External table). In order to provide better query speed a sequence may also be created for the MessageTrackingInfo table.

In some embodiments, this approach may include a separate table to keep track of archived messages. In various embodiments, the table may be designed to hold archived messages separately from the Online message table, i.e. Message Board. This reduces the size of the Online message table so that it proves the performance on accessing the main table.

In one or more embodiments, this approach may include a custom message tracking information table to keep track of archived messages. In various embodiments, it may be important to keep the main table (Online Message Table) free of unnecessary space allocations as that comes with an excessive number of messages. In some embodiments, once such space is allocated, it may take an additional step to make it small. That may take a bit of time. In some such embodiments, during this time, the table may not be available to users. In many embodiments, the current message view may be the most frequently accessed view, so it should remain accessible to users at all times. It may be preferable to keep it light, such as to improve overall performance of operations once again in the table. In some embodiments, it may be kept light by having a separate table that retains Offline messages would make the Online Message table relatively small.

In various embodiments, one or more approaches may be utilized to implement the second table offline. For example, one approach may be to use the Oracle External table feature and another approach may be to implement a real table for Offline messages. In some embodiments, the Oracle External table may provide easy access to messages dump files. In many embodiments, messages may be exported as dump files in the external table format so that they may be readily accessible in the Oracle table context. The dump files may act as tables in this case. In some embodiments, messages may be archived in an external table which is stored as a dump file. Some approaches may be to implement a real table for the offline messages. Messages may be exported as a data pump export compatible dump file. In some embodiments, one or more aspects of one or more UI designs described herein may be based on one or more aspects of Oracle External Table, such as to maintain compatibility and/or facilitate intuitive operation. In various embodiments, this application may display messages from two different tables, Message Board and Offline in one table view.

Messages may be fed into the Message Board table by applications as events occur. These messages may accumulate over time. Currently, this accumulation slows down the performance of the message viewing mechanism. The user often deletes them periodically to maintain the performance of the application. During an audit, auditors may ask for messages that may be related to certain audit records. If they may have been deleted, there may be no way of viewing these messages. The user would rather want to retain the message for a long period of time. This design may accommodate such user's requirements and still may have advantageous performance.

An existing Online (Message Board) table may be updated upon install of an updated message handling application, such as by the message controller, to take advantage of the Offline table. The user may have the choice of archiving old messages to dump files at that moment.

In some embodiments, it may be important to keep the Online table small enough to maintain superior performance. Once the database reaches a certain point, it may be desirable to export old messages to outside of the table. This may be where the Offline table comes in.

In this design, the user may automatically archive messages from the Online table to a dump file immediately on demand, or on a schedule. The user may schedule the range (interval) of the messages to move and when to archive them. Once messages may be archived, they may be removed from the Message Board table automatically. They may also be moved immediately on demand without a schedule. Each archive action creates external tables based on the archive range.

When such a move occurs, a new entry(s) for the archive dump file(s) may be created to record the move in the Message Tracking Information Entry table. Each entry retains relevant information about the messages that may have been exported from the Online. The entry has enough information to help key mechanisms to work efficiently. The entry also contains information that may be helpful to optimize the search performance of the view filter. The current view filer may be modified to take advantage of this information.

In some embodiments, messages may be exported out to locations on the server. In various embodiments, messages could be exported to totally separate locations. In many embodiments, messages may be exported to a default location.

In some embodiments, Oracle Directory may be used to export such dump files. The location of those files must be tracked by updating the message tracking entries that may be associated with the files. This may be not necessary for this release, but it may be designed for future extensions in mind. The entry line of each exported block may be updated to reflect such an operation and additional information may be added to the entry about the export operation.

Messages that may be exported into a dump file and they may be retrieved by executing SQL statements on the table. In other words, the dump file functions as the Offline table in this case. No real table needs to be implemented. The approach, Oracle External Table, has a few drawbacks, i.e. draw backs such as no indices may be allowed and dump files must reside on the server machine.

This application (e.g., message controller 104) has one view to show messages from the Online and Offline tables. A set of default view filters may be created for the view. View filters in this view should function as those that may be in Project Window and Configuration Manager do.

This application shows and manages messages in the different stage of their life cycle. It may carry over existing features to manage the page size and the password tabs. The purge tab, however, may not be carried over. In addition to those, new features may be added to export and import messages.

A message's life cycle consists of two different stages, Online and Offline (data structure, such as an Oracle External Table). There may be corresponding tables that retain messages at each respective stage as already briefed above. There may be only one table view that shows messages from these tables.

Managing messages may be another main feature of this application. Messages may be exported from the Online table. They may be imported (brought online) to the Offline table.

In the following sections, a possible UI design that implements these aspects of the application may be described.

This application has two main parts, the viewing mechanism (e.g., message viewer 222) and the message management mechanism (e.g., message manager 220). The viewing mechanism may be enhanced to retrieve messages from these two different tables and also to improve performance on such retrievals. Two levels of filter criteria may be implemented for the main view.

The first level may be to specify the boundary of each view filter search range using sequence numbers. The second level comes from filter conditions that the user specifies. The combination of these two level should limit the search range of the view filter.

The View Filter Editor may be available for the table view. A set of view filters may be created for the view per user. The same view filter may be used to accommodate two distinct usages, user specific and all users (privileged feature). Application based filtering may not be implemented in the mechanism itself. If that may be required, each user should create such view filters.

The view has a set of view filters per user. Once a view filter may be created for a view, the user may apply it to show messages. This may be done in the same manner that may be implemented in Project Window and Configuration Manager. When the application opens, view filters that may have been created by the user and that may be publicly available may be listed in the Filter By combo box.

As previously mentioned, in several embodiments, filter conditions may be supplied as parameters. In various embodiments, the view filter code may be able to accept parameters. In various such embodiments, the paging mechanism used in Configuration Manager and Project Window may be adopted to accept parameters. In some embodiments, a paging feature compatible with Oracle may be used to accept parameters.

Messages, once generated, must be managed. The user should be able to archive them and use them for viewing. These actions may be implemented in the Messages view's properties tool.

In many embodiments, the user may be able to archive messages from the Online table immediately and/or automatically, such as based on a schedule. In one or more embodiments, messages may be removed from the Online table as they are archived to the outside of the database in the binary form. In some embodiments, archived messages may be read and displayed in the main view table of the application.

Figure 4A:
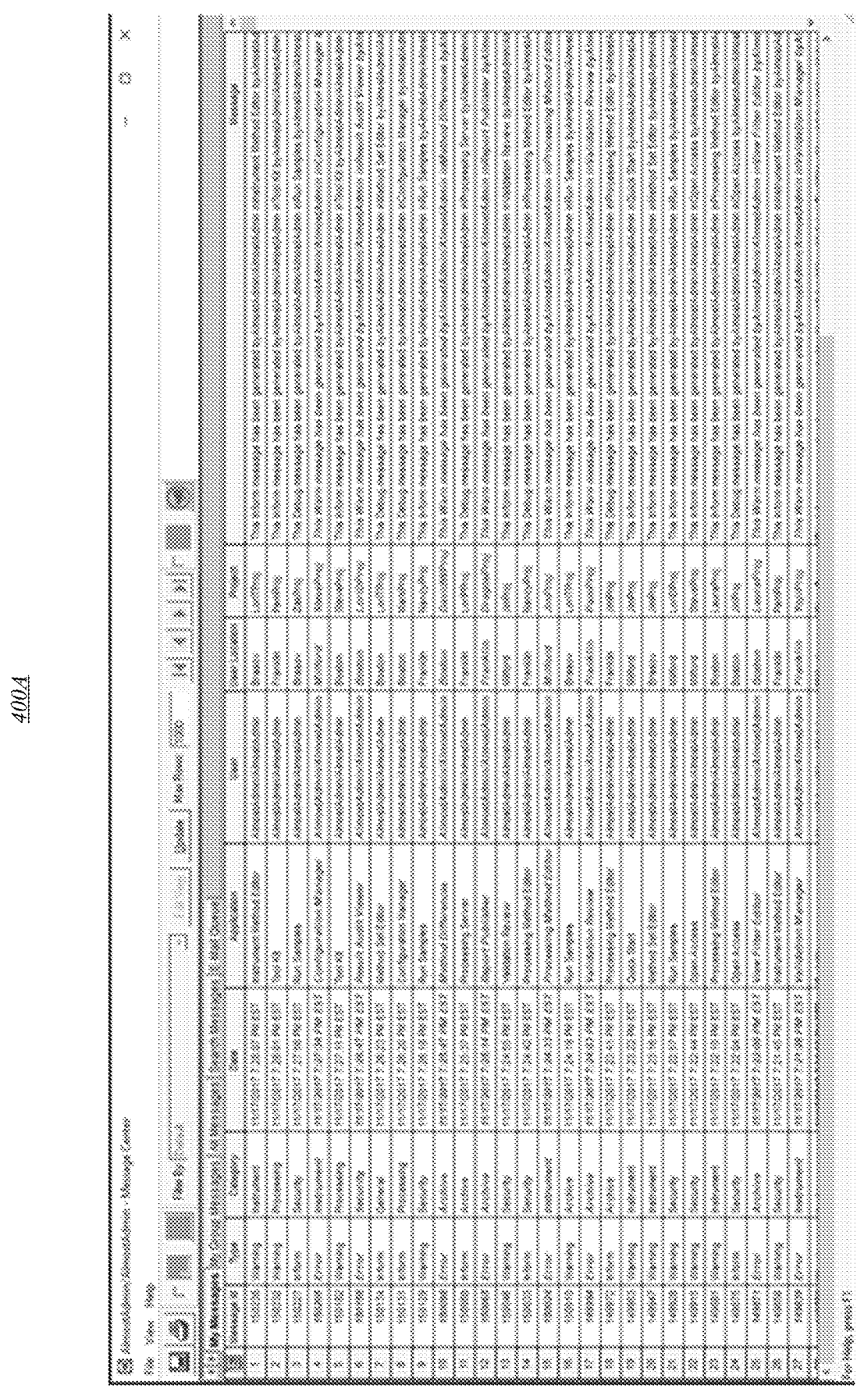
Figure 4B:
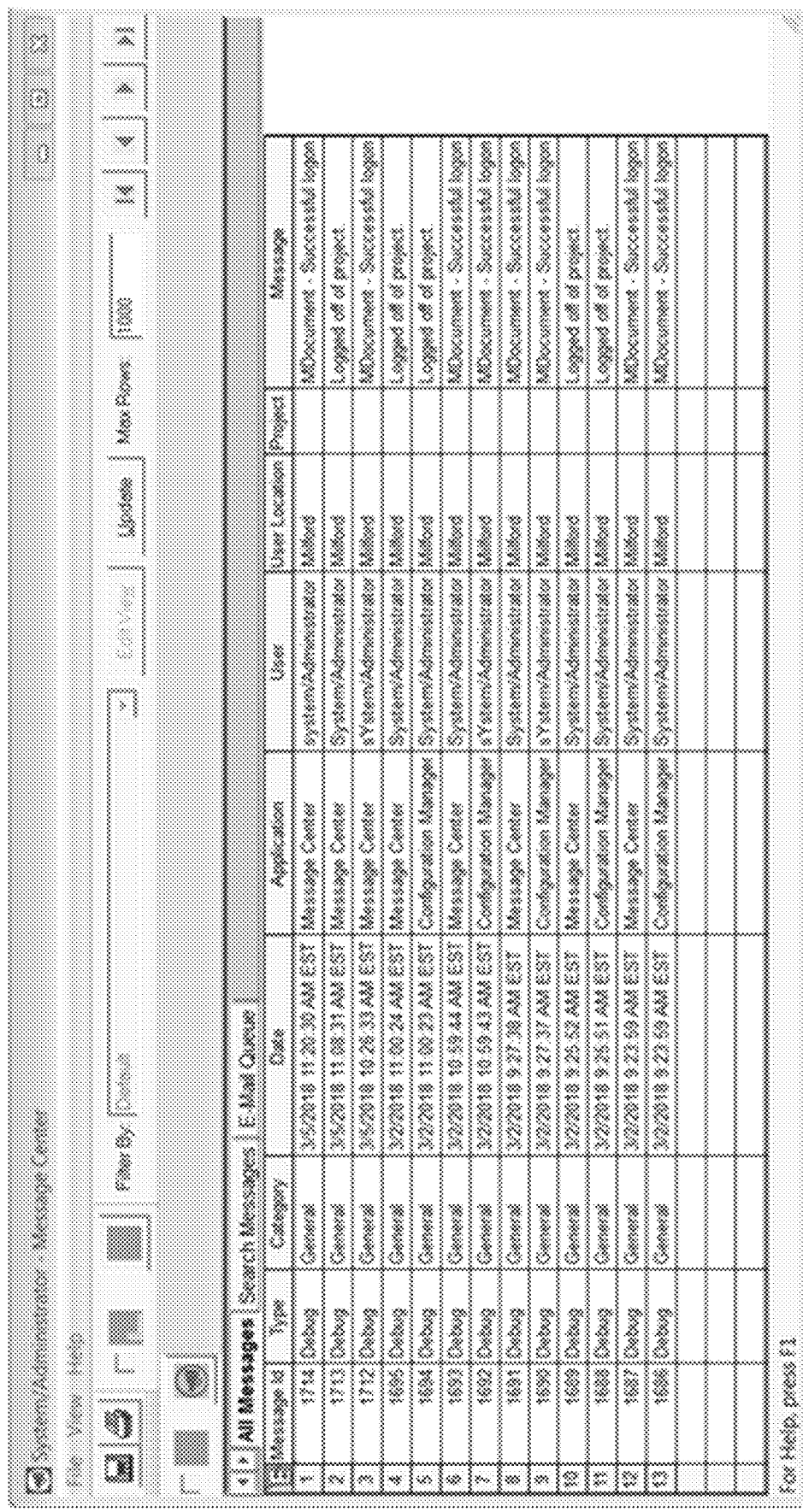

FIGS. 4A and 4B illustrate exemplary aspects of a message center according to one or more embodiment described herein. In various embodiments, the view filter editor may form one or more portions of message controller 104, such as by being incorporated in and/or implemented by message viewer 222. In some embodiments, message controller 104 may include a message center application. Embodiments are not limited in this context.

In various embodiments, the message center application may present a list of generated messages in 5 different views (tabs): "My Messages", "My Group Messages", "All Messages", "Search Messages", and "E-Mail Queue". There may be three different possible tab layouts which may be seen depending on the privileges for the logged in user/user type. Users without the "Administrator" privilege, but with the privilege "View Message Center for All Users" may see all 5 tabs. Users without the "Administrator" privilege or the privilege "View Message Center for All Users" may see 3 tabs: "My Messages", "Search Messages", and "E-Mail Queue". Users with the "Administrator" privilege may see 3 tabs: "All Messages", "Search Messages", and "E-Mail Queue".

In various embodiments, the Message Center messages views show a Date column, a "Message Id" column that shows a unique id for each message, and another column called "User Location." In many embodiments, the message center email queue view may include a message center email tab. In several embodiments, there may be a new E-Mail Id column that shows a unique id for each email message.

When the Message Center application may be opened, the title bar of the Message Center window may include the name of the user that opened the application along with that user's user type (e.g., privilege level).

In many embodiments, one or more of the following menu items may available in the Message Center application:

In some embodiments, File: Save As File may save the current view of the Message Center as a text file. This menu item may be grayed out when there are no rows in the selected view. In various embodiments, File: Print Table may print the current view of the Message Center. This menu item may be grayed out when there may be no rows in the selected view. In some embodiments, File: Close may close the Message Center window.

View (The menu items that may be present may match the tabs seen in the Message Center): My Messages—selecting this may change the view to "My Messages". View: My Group Messages—selecting this may change the view to "My Group Messages". View: All Messages—selecting this may change the view to "All Messages". View: Search Messages—selecting this may change the view to "Search Messages". View: Email Queue—selecting this may change the view to "Email Queue".

The following toolbars may be shown/hidden when selected/unselected in the View menu: Toolbar (save and print buttons—these buttons may be grayed out when there may be no rows in the selected view); Status Bar (shows or hides the status bar); View Filter Bar (filter by combo box, edit and update buttons, max rows box, first, previous, next, last buttons); JIT View Filter (two buttons: Use saved JIT view filter, Save JIT view filter dialog); Message Center Bar (two buttons: Nearline button with checkbox and Message Center button). View: Update—selecting this may update the current view Help: Help Topics; About Message Center. In some embodiments, one or more of the following right-click menu items may be available in the Message Center table: Copy—copies the selected rows in the table as text or a text file. Hide Column—disabled for this version. Show All Columns—shows all Message Center columns. This option may be enabled only after a column may be hidden using the Table Properties window. Print Table—prints the current view of the Message Center Table. Table Properties—allows the user to adjust the visual properties of the table for the current open session of Message Center. Column Properties.

In some embodiments, pressing the F1 button, when in the Message Center window, may open a context sensitive topic called "Message Center."

In many embodiments, in the Message Center window, there may be two buttons: "Nearline" and "Message Center". Each may have a tool tip: "Include Nearline Messages" and "Show Latest Messages". By default, the "Nearline" button may be not checked, and may be grayed out in all views except the "Search Messages" view.

In many embodiments, in addition, or alternatively, to using the menu selections, the user may move between the message center views by clicking in the tab name.

The "Search Messages" view may be where the view filter mechanism can be implemented. In some embodiments, View Filters may be not available in any of the other views. In the "My Messages", "My Group Messages", "All Messages", and "Email Queue" views, the View Filter combo box and all buttons in the View Filter toolbar may be grayed out except the four paging buttons, max rows, and the Update button. In the "Search Messages" view, the View Filter combo box and all buttons in the View Filter toolbar may be enabled.

The "Update" button may be used to update the current view with new entries. New entries may not automatically be added to the views.

In the "Search Messages" view, the view filter combo box lists only view filters that may be available to the user (all default and public view filters plus all private view filters owned by the user). Private view filters not owned by the user may be not available in the combo box list.

The view filtering mechanism may be available in the "Search Messages" view of the Message Center application. Its functionality may be basically the same as that in Project Window and Configuration Manager, except for three changes that were specifically added to the mechanism for the Message Center application. One may be an enhancement and the other two may be restrictions.

The enhancement has been already discussed above. The Nearline button may be used to exclude all nearline tables from the search. Adding view filter conditions in the date and/or id column may be also used to exclude some or all the external (nearline) tables prior to applying the view filter.

External table filtering may reduce the number of external tables that the view filter mechanism needs to include for filtering. Each external table (i.e. message groups) contains messages with a specific date range and a specific id range. If the date or id conditions in the view filter do not fall inside the date or time ranges of an external table, that external table may not be searched. This step should improve the performance of the view filters when nearline tables may be included in the search.

One restriction that needs to be in place for Message center view filtering. The SQL statement that the view filter constructs may be rather complicated considering it may be constructed using a UNION operator to combine multiple SQL statements each of which may be designed to filter messages from a particular online or nearline table. For example, if there may be 10 external tables, SQL statements for 11 tables must be combined into one (including the online table (i.e. Message Board table). Due to this additional complexity the "GROUP BY" mechanism may be not available in Message Center and "Group By" may be not available in the right click menu in the table in the Message Center's View Filter editor.

The second restriction may be that the user cannot successfully apply a view filter that has multiple columns of the same name when including Nearline messages. For example, a view filter that contains multiple columns called "Message id", may fail when accessing Nearline messages due to the complication that comes from the UNION logic mentioned above. If the user applies a view filter with duplicate columns to Nearline messages, there may be a popup error message stating something like "Duplicate column names not allowed when searching Nearline tables." This functionality still works for accessing Online messages.

Other than these two exceptions, view filtering works in Message Center as it does in the project window.

While a view filter may be being applied, the "Update" button temporarily changes to read "Cancel". It also changes to "Cancel" when changing views from "My Messages" to "All Messages" while switching if there may be a lot of messages in "All Messages" view. As soon as the view filtering may be complete, the button changes back to "Update". If the user clicks "Cancel", filtering may be canceled and either an incomplete list of filter messages or no messages may be displayed in the table.

In various embodiments a paging mechanism may be implemented. Message Center may utilize the same paging mechanism to view messages as in Project Window and Configuration Manager. Pages of x messages, where x=the number of Max Rows, may be able to be viewed page by page. If x> the number of viewed messages, all messages in the current view may be shown on a single page. The default value for x may be 1,000; the allowed values for x range from 0 to 10,000.

In some embodiments, a quick sort may be performed by clicking on the column header. In some such embodiments, doing a quick sort by clicking on the column header may only sort the messages that are being viewed in the table for that current page.

In many embodiments, similar to in the Project Window and Configuration Manager, there may also be "First Page," "Previous Page," "Next Page," and "Last Page" buttons with the Max Rows box. The "First Page" button may have a corresponding tooltip that displays "Display First Page." The "Previous Page" button may have a corresponding tooltip that displays "Display Previous Page." The "Next Page" button may have a corresponding tooltip that displays "Display Next Page." And the "Last Page" button may have a corresponding tooltip that displays "Display Last Page."

In several embodiments, when the "First Page" button is pressed, the first page's worth of messages may be displayed in the message table, ordered by the view filter condition. The number of messages viewed on a single page may be again determined by the Max Rows value that the user specifies. When the number of max rows is greater than the number of messages viewed then all messages may be displayed.

In various embodiments, when the "Previous Page" button is pressed, messages equal to the number of Max Rows may be displayed starting from the first previous message before the first message displayed in the current view. For example, if the default view filter has been applied to the Messages with Max Rows=1,000, and messages 2,001-3,000 may be currently viewed in the table, when the "Previous Page" button may be pressed, then messages 1,001-2,000 may be displayed.

In some embodiments, when the "Next Page" button is pressed, messages equal to the number of Max Rows may be displayed starting from the next message after the last message from the previous page. If the number of messages to display may be less than the number of Max Rows, then all remaining messages may be displayed.

In various embodiments, a user location column may be included. All Message Center views may have the user location column except for the "E-Mail Queue" view. The user location column may be called "User Location", by default, it may be located after the "User" column and before "Project" column.

In many embodiments, when the "Last Page" button is pressed, the last page of messages may be shown in the message table. This may list the last x number of messages in the table, where x may be the number of rows that may be set in the Max Rows text box.

In various embodiments, the user may change the Max Rows value at any time. In some embodiments, when the value is changed and the "Update" button clicked, the page may take on the new size. After updating, the first message of the page (determined by the current view filter) may be set as the new 'first' row and a page equal to the number of Max Rows may be shown. The page navigation buttons may then be used again as described above. The "User Location" column may be included when creating a view filter in Message Center by using the View Filter Editor and by the View Filter Wizard.

In several embodiments, the "User Location" field may report the user's location at the time when the message was generated. In some embodiments, changes to the user's location in the user properties may apply to newly created messages in the Message Center, after the change occurs. When no location is associated with the user, the column data cell may be empty. Messages generated by non-users (WatersEmailService and AutoArchive) may have a User Location, and that field may appear blank.

In various embodiments, the Message Center may provide and/or have a plurality of views, although each of the views may not always be visible. For instance, the Message Center may provide and/or have five views. The first three views may be designed to display only the online messages (recent messages). In some embodiments, the first three views may be called My Messages, My Group Messages, and All Messages, respectively. The fourth view may display both online and nearline messages and may be designed to provide the view filtering capability. In some embodiments, the forth view may be called Search Messages. The fifth view may enable a user to view emails that may be pending, sent, or failed in error. In some embodiments, the fifth view may be called E-Mail Queue. In various embodiments, all views, or a subset thereof, may be read only views and no messages or email notifications may be manually deleted by the user.

In many embodiments, because preferences may be not saved for the Message Center, the current state of Message Center may be not saved when the Message Center process ends. In several embodiments, every time the Message Center process is started, all settings may go back to their default state. For instance, the default states may include one or more of: (1) Max Row may be set to 1000; (2) the default view filter may be set to Default; (3) the default view for the My Messages view, for users with the Administrator privilege, the default view may be the All Messages view; (4) the Nearline button may be unchecked; and (5) paging starts from the first page.

In various embodiments, recent Messages Views may include one or more of My Messages, My Group Messages, All Messages. In some embodiments, by default, messages may be shown in the descending order starting with the most recent one at the top in these views. Each view may have its own default view filter called Default. In some embodiments, the Default view filter for the My Messages view may display all the messages for the current user's user name. In some such embodiments, this may occur no matter what user type these messages have.

In several embodiments, the Default view filter for the My Group Messages view also may have a canned filter condition designed to fetch all the messages that belong to all users in the groups to which the current user belongs. In many embodiments, the Default view filter for the All Messages view may not have any filter conditions. Accordingly, it may be designed to fetch all messages from all users.

In one or more embodiments, the Search Messages View may provide the view filtering mechanism. In some embodiments, when the user does not may have the privilege "View Message Center for All Users", the "Search Messages" view (using the 'Default' view filter) contains only that user's messages, and therefore only those messages may be available for searching. When the user has the privilege "View Message Center for All Users", the "Search Messages" view (using the 'Default' view filter) contains all messages and all messages may be available for searching.

In various embodiments, the E-Mail Queue View may show a log of email messages. The messages seen may depend upon the user's user type privilege for "View Messages for All Users". If the user has the privilege, messages from all users may be listed. If the user does not may have the privilege, messages for that user's user account name only and not the user/user type may be listed.

In several embodiments, the following rules may apply to one or more of the plurality of views discussed herein. The current view filter selection, the state of the Nearline button, the Max Rows value, and the page position may be all preserved during the current session (i.e., while the Message Center process remains active). In some embodiments, an exception to this rule may be that the page position of the 'My Messages' view (and the 'All Messages' view for user types with the Administrator privilege) reverts to the first page (in order to display any new messages). Once the Message Center process ends, the settings may be no longer preserved and when the Message Center process starts up in the next session, they go back to Default settings.

In some embodiments, this application may have the look and feel of Project Window. It has a menu bar, a toolbar and two dialog bars. A few menu bar items may be also available in the toolbar for quick user actions. One of dialog bars may be for the view filter and paging mechanisms. The other dialog bar may be for managing temporary just in time view filters. The user launches the View Filter Editor by pressing the Edit View button. The paging dialog bar works the same as it does in Project Window.

In various embodiments, there may be a new dialog bar that hosts a check box that allows the user to view Offline messages. When this check box may be on, Offline messages may also be displayed along with Online messages based on the filter conditions of the view filter.

FIGS. 5A-5D illustrate exemplary aspects of a view filter editor according to one or more embodiments described herein. In various embodiments, the view filter editor may form one or more portions of message controller 104, such as by being incorporated in and/or implemented by message viewer 222. In some embodiments, view filter editor may assist in the creates of filters, such as for searching online and/or offline messages. Embodiments are not limited in this context.

The View Filter Editor may be accessed from the "Edit View" button in the View Filter Bar. The View Filter Editor opens with the view filter that may be currently selected in the combo box. A view filter type, "Message Center", may be introduced for the creation of view filters for viewing the Message Center messages. That may be the only choice available for Message Center in the dropdown. The functionality of this editor works the same as that in Project window and Configuration Manager.

The user may create and save view filters and may choose any view filter from the combo box to retrieve either online or nearline messages or both. The "Include Nearline Messages" checkbox must be checked in the search view before applying a view filter, to include nearline tables messages as well as online messages in the search view. When the checkbox may be not checked, the search view may only contain online messages.

All fields applicable to Message Center appear in the view filter editor. They may be Application, Category, Date, Message, Message Id, Project, Type, User, and User Location. The Category column may be a dropdown which includes the following message categories: General, Archive, Instrument, Security, Processing, Email and =#. The Type column may be a dropdown which includes the following message types: Inform, Warning, Error, and =#. Columns may be added and deleted from the table in the view filter editor.

The Date and Message Id columns may be used as normal filters for online messages but may also be used to filter out the nearline tables that may be not of interest in the search, prior to the application of the view filter when the "Include Nearline Messages" checkbox may be checked. If there may be any view filter row without a condition on either the Date or Message Id column when the "Include Nearline Messages" checkbox may be checked, all nearline tables may be used for view filtering. This may affect the performance of the search.

The AND/OR conditions for view filtering may work exactly the same as they do in the Project Window. The current functionality for using AND conditions in the editor may continue to work when used in the same cell or the same row in the table. The current functionality for using OR conditions in the editor may continue to work when used in the same cell or when using multiple rows in the table. The user may have to be conscientious of how they use AND/OR conditions (and the "Include Nearline Messages" checkbox) when setting up a view filter that includes nearline tables to ensure they may be using the intended tables; otherwise, the user could expect to see a drop-in performance when loading the results of a filtered search that includes millions of messages being loaded to the Message Center search view, when the "Include Nearline Messages" checkbox may be checked. View filters which may be created for the Message Center may be deleted using the file menu item in the Message Center's view filter editor.

Figure 5A:
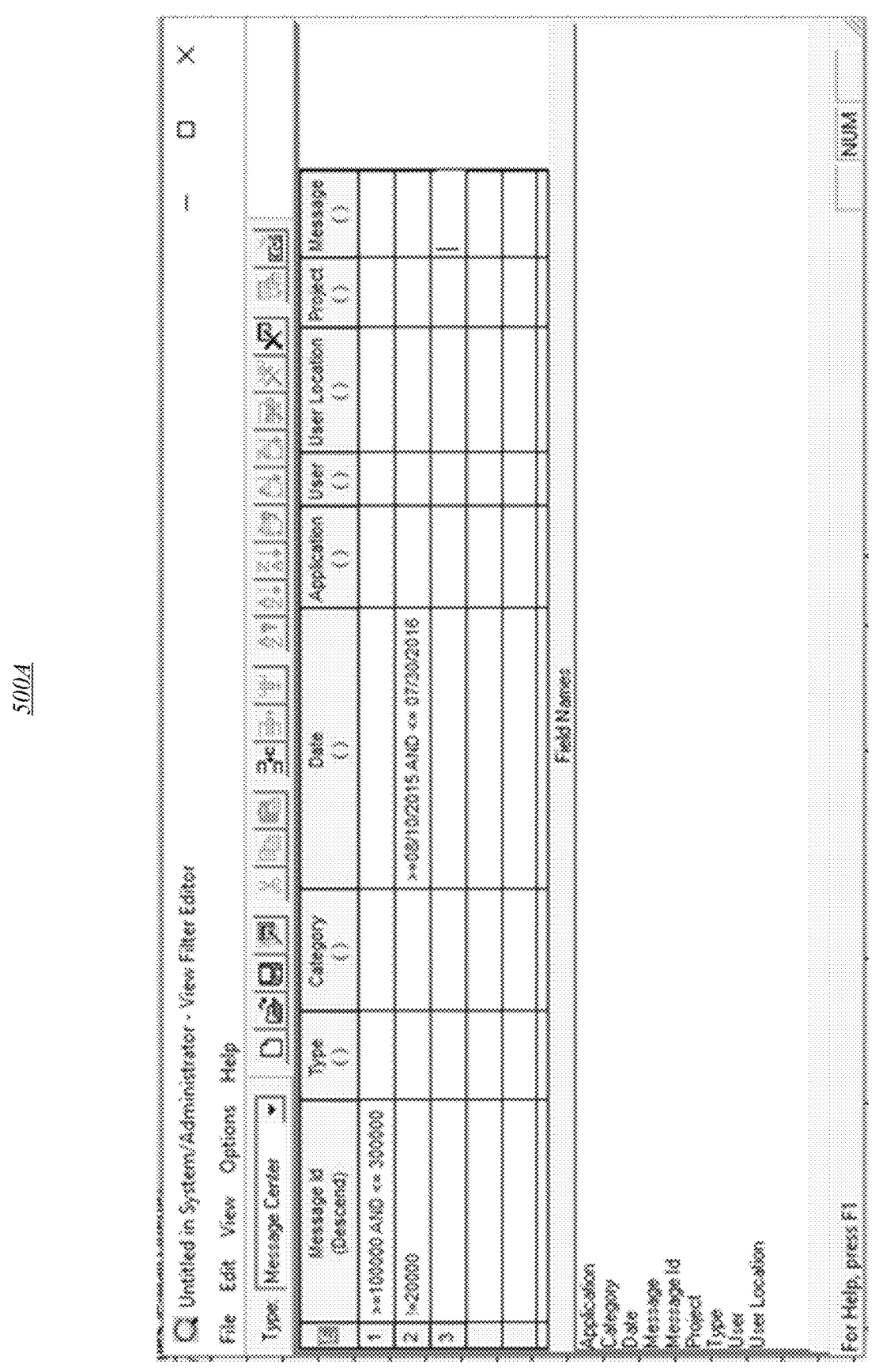
Figure 5B:
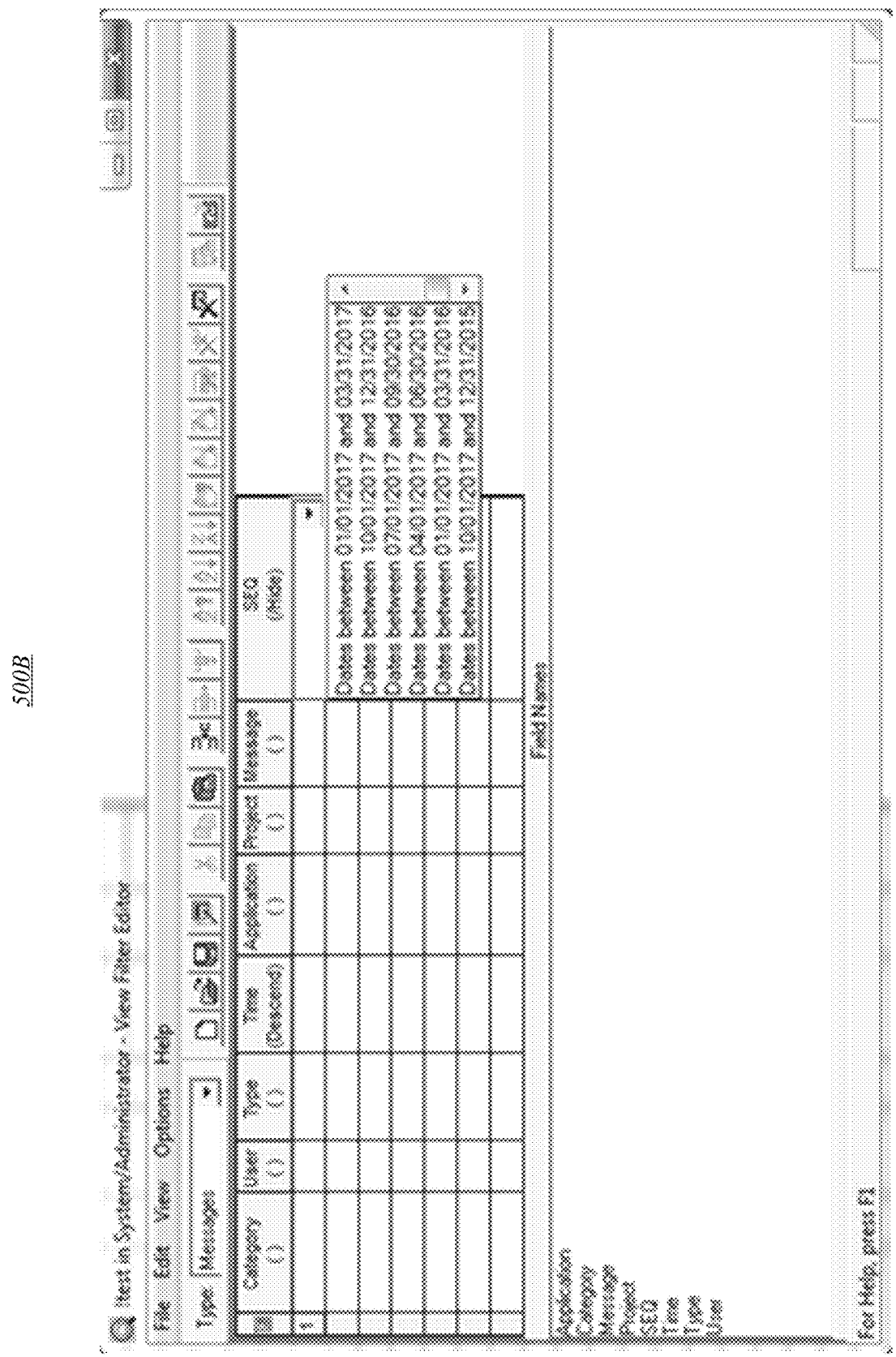
Figure 5C:
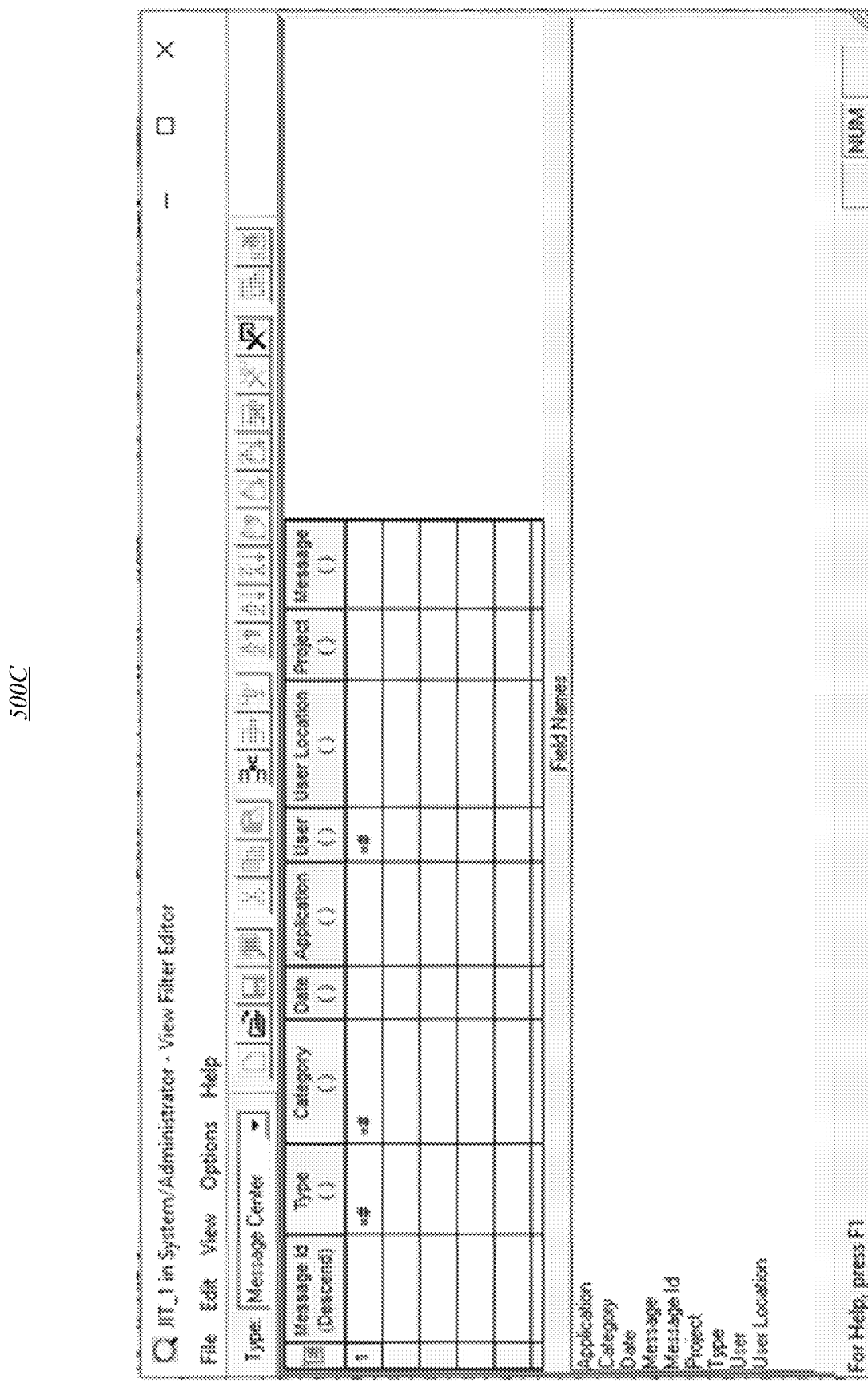
Figure 5D:
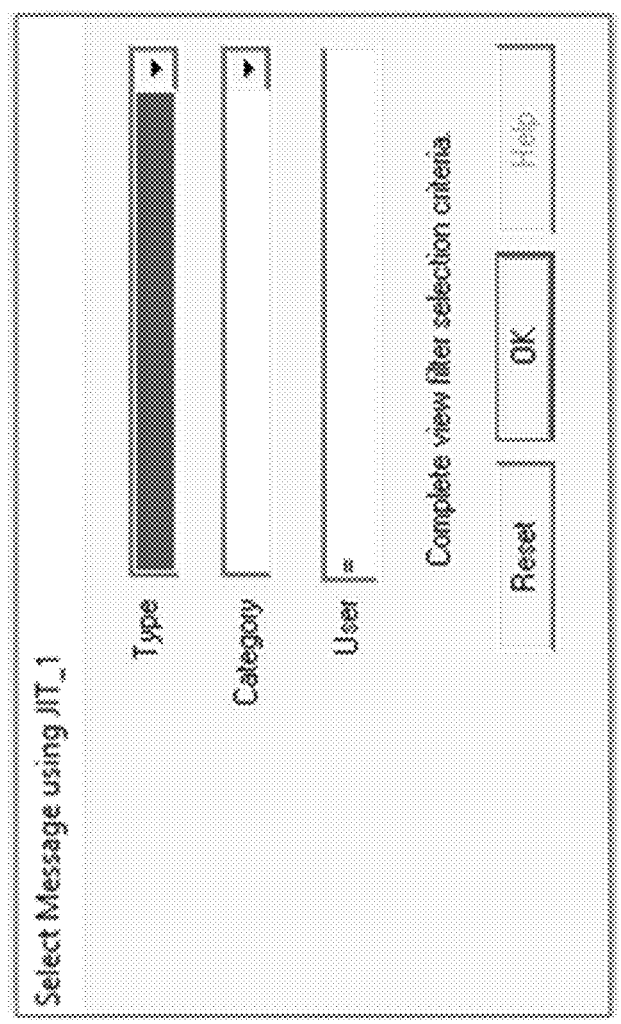

Referring more specifically to FIGS. 5C and 5D, when applying a View Filter that was setup with a keyword, "=#", as seen in the picture above, the application pops up the "Select Message using 'view filter name'" dialog seen below. The Just In Time (JIT) View Filter tool bar may be enabled when the current view filter has a Just In Time filtering criteria.

The JIT View Filter toolbar contains 2 buttons:

"Use saved JIT View Filter" check box—once enabled may temporarily save the current criteria and give user the ability to use the Update button to refresh the view without again filling/selecting criteria. To alter the current JIT criteria, uncheck the "Use saved JIT View Filter" check box and press the Update button.

"Save JIT View Filter"—this may open the save View Filter dialog. After the user provides a name, the current JIT View Filter may be saved (with the current JIT criteria) as a distinct View Filter. Once the view filter may be saved, the JIT View Filter toolbar bar may be disabled because the current view filter may be no longer a JIT view filter.

In the "Select Message using 'view_filter_name'" dialog, if the Reset button may be pressed the current JIT criteria may be discarded and the user may fill/select new criteria. Pressing OK without any criteria may display all messages and the JIT View Filter toolbar may be disabled.

In the "Search Messages" view, the default view filters are: "Default", "Default General", "Default Process", "Default Security", and "Default Acquisition". The "Default" view filter does not filter out any messages; "Default General" shows only messages with the category "General"; "Default Process" shows only messages with the category "Processing"; "Default Security" shows only messages with the category "Security"; and "Default Acquisition" shows only messages with the category "Acquisition".

These default view filters may be the basis of any new view filter, but they cannot be modified. These view filters may be only available from the View Filter combo box. They cannot be picked in the View Filter Open/Save dialogs. If the user tries to save a view filter with any of the default names, it may be rejected.

In some embodiments, it has been found that the sequence numbers of the table may be a better alternative to dates when used as filter conditions to limit the search range. Each row of the Message Tracking Information Entry Table may retain the sequence numbers of both the top and bottom messages along with the dates of those messages. This may be this way so that the range of the messages that may be archived may be easily identified.

These sequence numbers may be used to determine the search range of targeted messages when a view filter specifies a block or dates in its filter condition clause. This so-called partition like access restriction using the sequence number in the view filter mechanism should improve the performance of the view filter SQL statements. This means that the user may be able to specify a message block(s) when editing a view filter.

In various embodiments, a way of building a view filter statement may be introduced in order to incorporate multiple external tables into the mechanism.

In some embodiments, the View Filter class may be arranged to show the online messages from the Message Board in Configuration Manger. In some such embodiments, the message view may be implemented in a separate application instead. In various embodiments, in order to utilize the Message Tracking Information Entries in the view filtering mechanism, it may be necessary for the information to be readily available when a SQL statement may be constructed. When the user specifies a date as a filter condition, it may be used to automatically set up sequence ranges for the search. They may be supplied as a filter conditions. If multiple dates may be used, multiple sequence ranges may be applied to the SQL statement automatically by the View Filter mechanism.

In order to utilize Message Tracking Information Entries in the view filtering mechanism, the list must be retrieved at least once. When it becomes big, it may affect the performance of view filtering. To alleviate such situation, a stored procedure may be written to retrieve Message Tracking Entries to improve the performance on the initial access to the table by the application. Once the list may be retrieved it should exists while the application may be running. The size of the table may not become too big. Even when the user moves messages every 3 days, only 120 entries may be created per year. In 30 years, it may add up to 3600 entries.

In order to retrieve external table names from view filter's condition clause, the view filter class may be modified to identify external tables automatically and build one SQL statement based on them. This may be implemented as an outer layer of the existing BuildStatement function. Here, the same view filter may be applied to the Online table as well as all external tables that constitute the view. The same view filter may be joined together using the UNION command. One execution of this combined SQL statement may retrieve message rows from all tables involved.

The external tables that may be identified during this process may be kept in the view filter so that they don't need to be regenerated until the Message Tracking Information Entry list may be updated.

A new class may be implemented to access this object. This object gets created when a block of messages may be archived from the Online table. The top and bottom dates of message blocks get converted to sequence numbers and stored along with the dates into this object as the block gets transferred.

Both the Start Date and the End Date of the block may be recorded when it may be archived from the Online table. Corresponding sequence numbers may be also recorded.

As messages may be archived, they get deleted from the Online. They may not be deleted until the dump file may be created.

The Active flag may be used to indicate a dump file may be now loaded onto the external Offline table or not. This flag may be set to true when an external table may be constructed from the dump file and ready for use.

The BeingArchived flag may be set when archiving starts and then may be reset when it may be done. No message tracking information line should may have this flag set. If it may be set, archiving of a particular message block could may have been failed.

The Not Used flag may be set when the user want to make a particular message tracking information row invalid. This could be used when a new Archiving schedule may be set to replace the failed attempt.

The name of the dump file may be automatically generated from the date range and the server name.

The data members may include one or more of: (1) Seq: The sequence of the current message tracking info (2) BeingArchived: This flag may be set while messages may be being archived. One it may be done, this may be reset. (3) Active: To indicate an external table may be created from the dump file and ready for use. (4) Start Date: The start date of the message block (5) End Date: The end date of the message block (6) Start Sequence: The start sequence of the message block (7) End Sequence: The end sequence of the message block (8) Dump File Location: The location of the dump file. (on the database server) (9) Dump file name: The name of the dump file. Automatically generated. (10) Dump file type: Binary. Note: CVS files may be not tracked. (11) Dump file size: The size of the dump file Inputs to the Message Board table may be made by applications as relevant events occurs. These inputs (messages) may be shown in a view. Messages may be archived as a dump file and they may be shown in the main view.

Figure 6A:
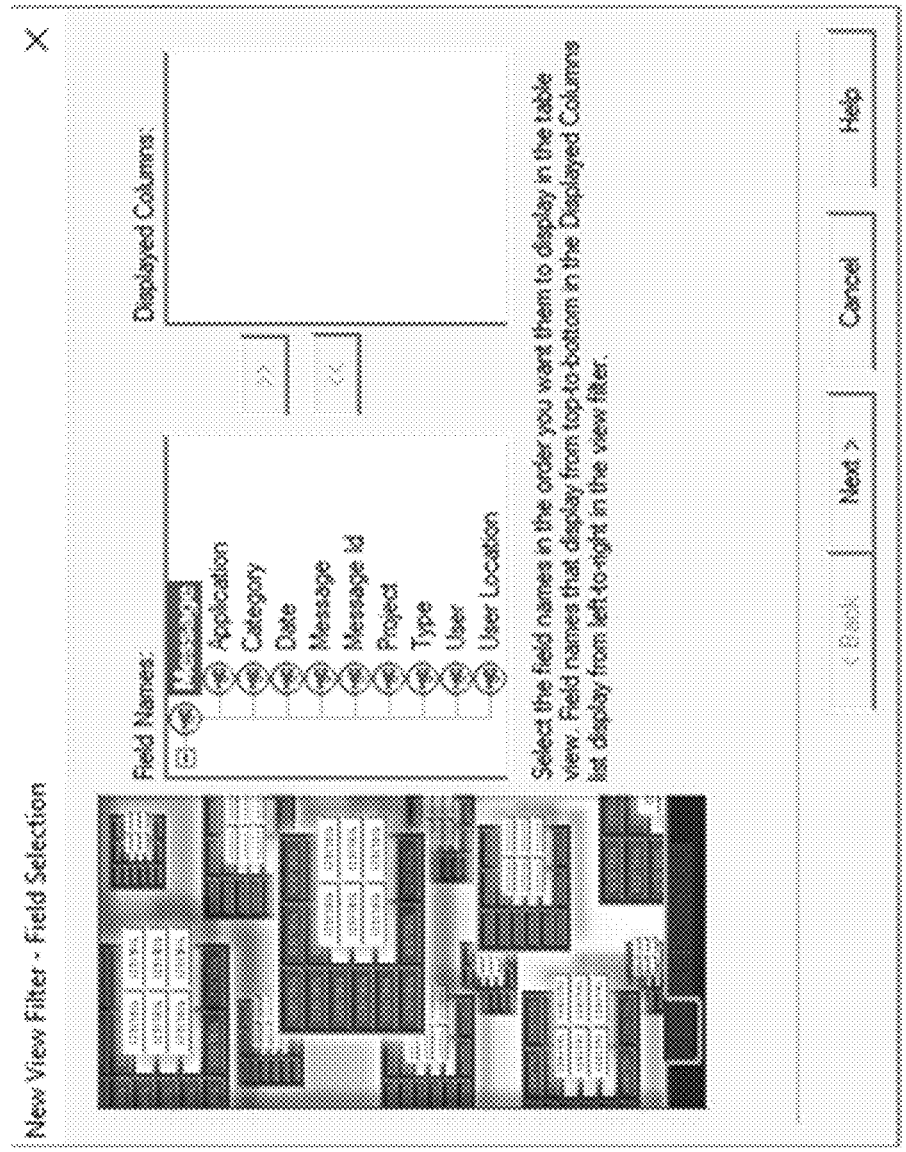
FIGS. 6A and 6B illustrate exemplary aspects of a view filter wizard according to one or more embodiments described herein.
Figure 6B:
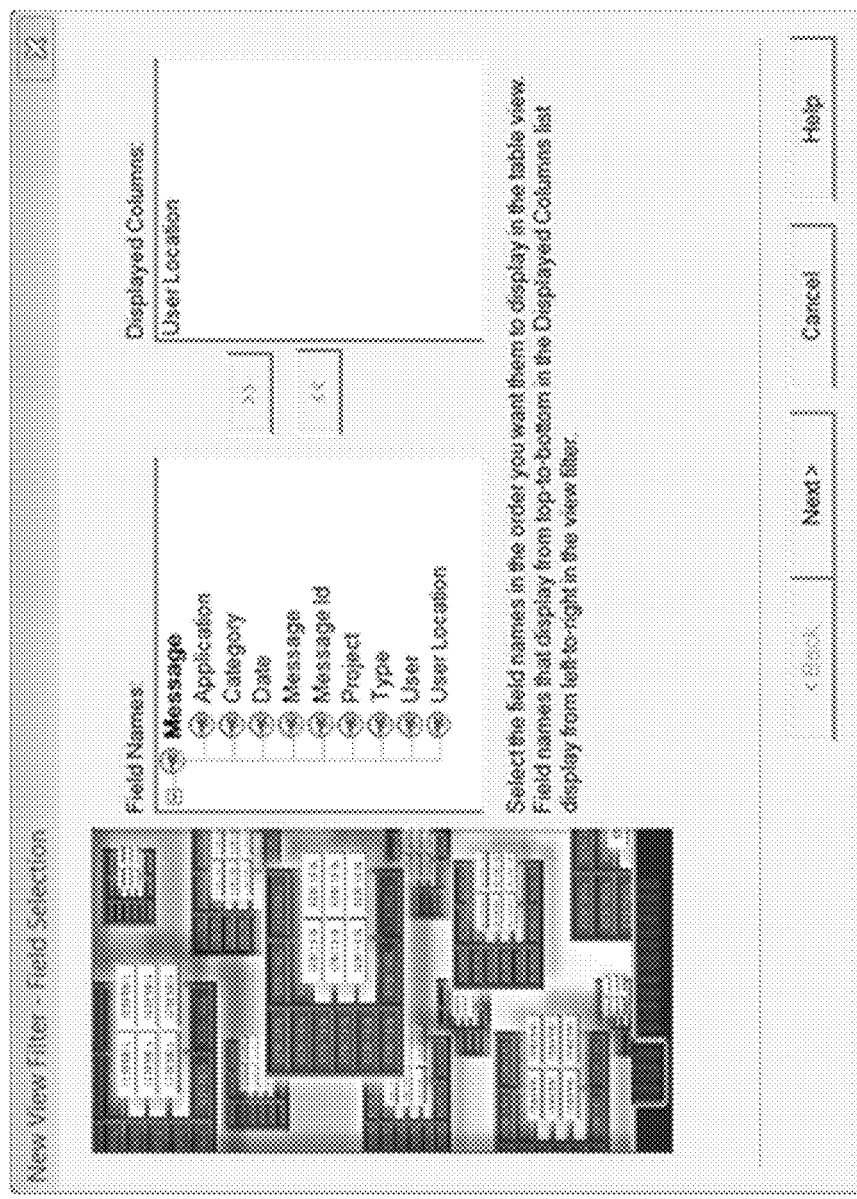

FIGS. 6A and 6B illustrate exemplary aspects of a view filter wizard according to one or more embodiments described herein. In various embodiments, the view filter wizard may form one or more portions of message controller 104, such as by being incorporated in and/or implemented by message viewer 222. Embodiments are not limited in this context.

In some embodiments, the View Filter Wizard may be selected from the View Filter Editor using the context menu or from the toolbar button. The first screen of the wizard contains the field names for the columns which may be displayed in the message center search view. The message center fields which may be selected from the Field Selection page may be Application, Category, Date, Message, Message Id, Project, Type, User, and User Location. The functionality of this wizard may be identical to that of Project Window and Configuration Manager.

In various embodiments, the text on the first page of the view filter wizard may read "Select the field names in the order for display in the table view. Field names that display from top-to-bottom in the Displayed Columns list display from left-to-right in the view filter." In various such embodiments, this text may be presented on the first page in the view filter wizard for Message Center, Configuration Manager, and Project Window.

Figure 7A:
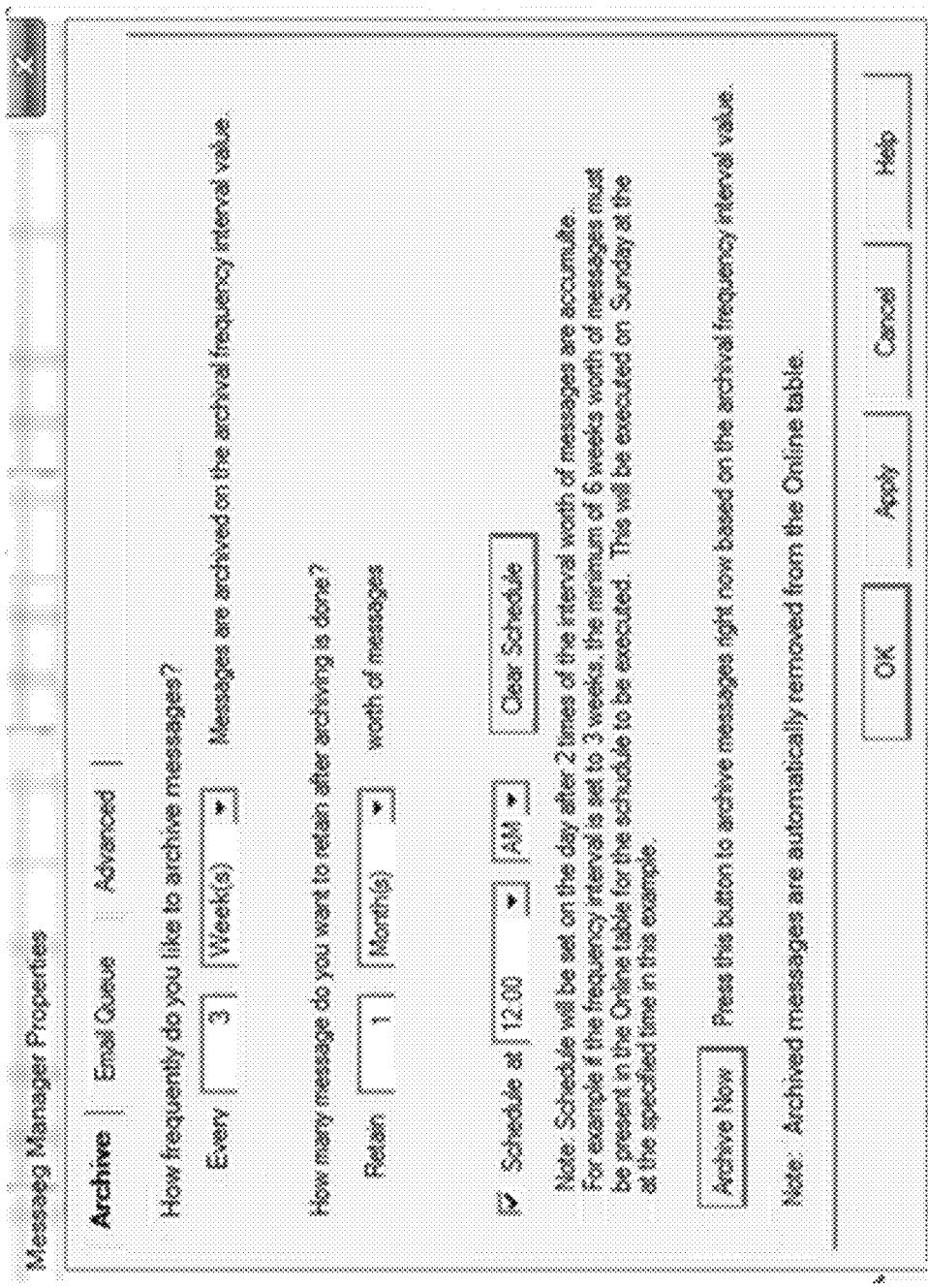
FIGS. 7A-7C illustrate exemplary aspects of message manager properties according to one or more embodiments described herein.
Figure 7B:
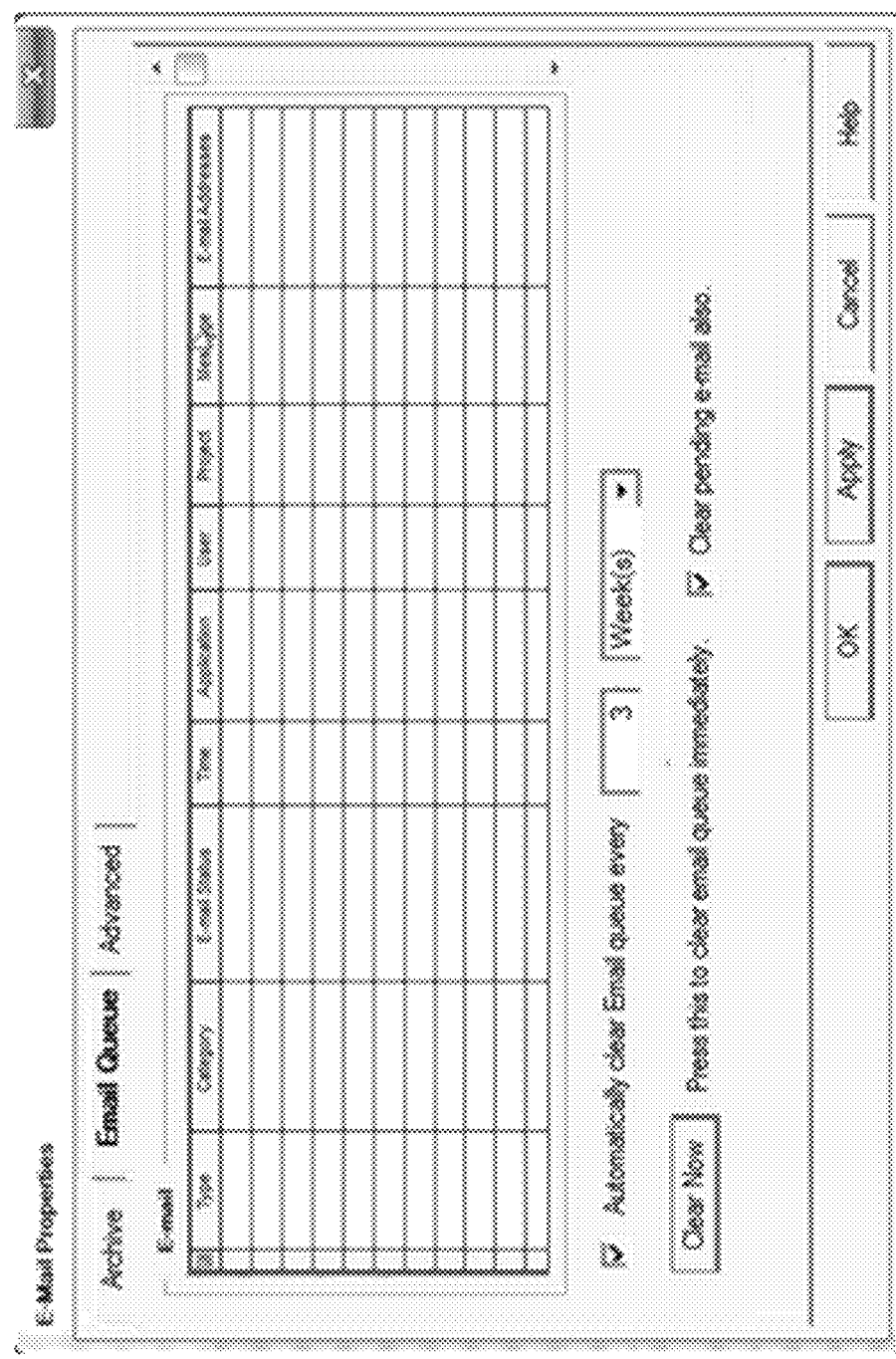
Figure 7C:
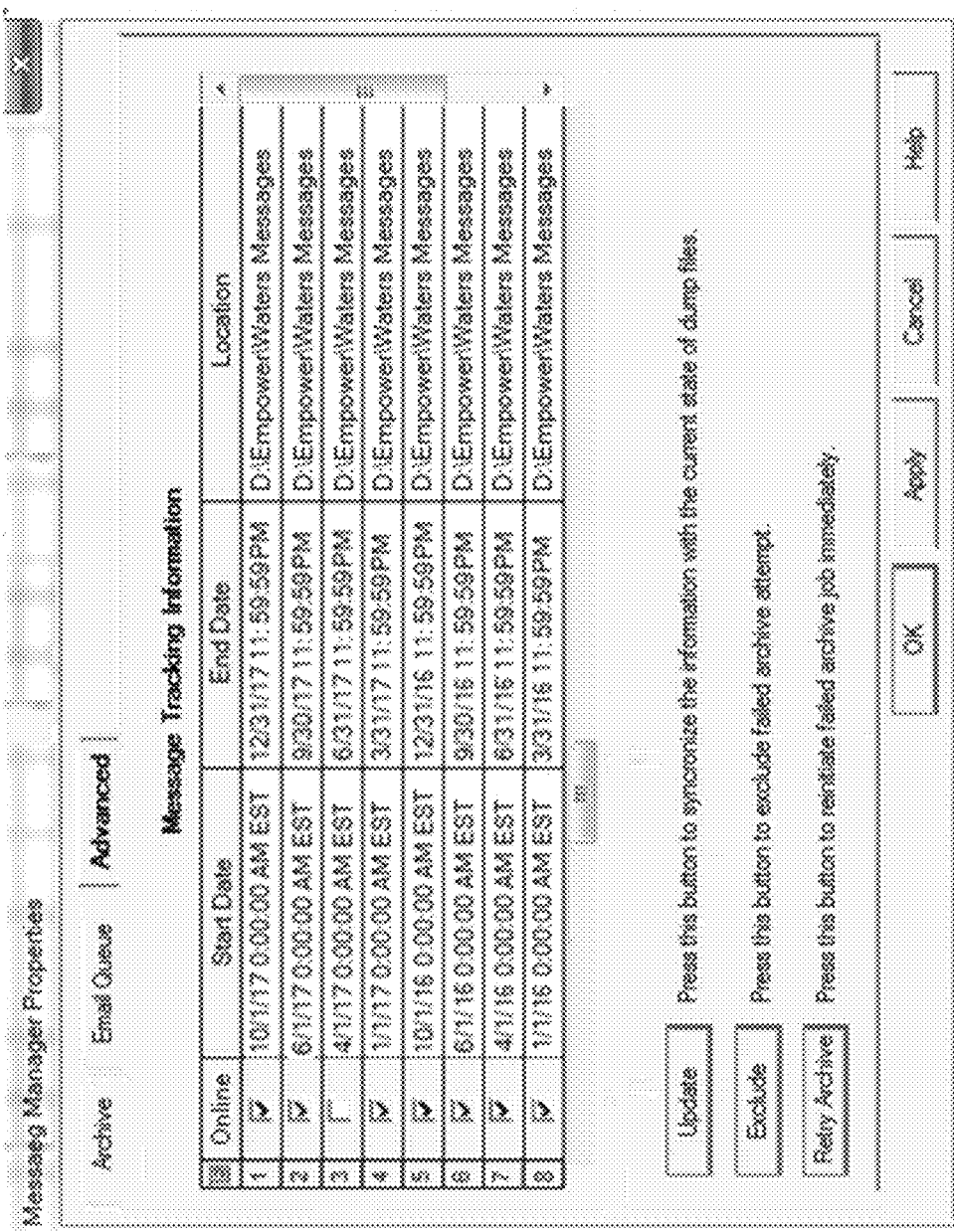

FIGS. 7A-7C illustrate exemplary aspects of message manager properties according to one or more embodiments described herein. In various embodiments, the message manager properties may be associated with user defined settings of message controller 104, such as rules for the generation of immediate attention messages 114 or archiving online messages 108 as offline messages 112. Embodiments are not limited in this context.

New Message Center application moves on-line messages to external tables automatically through an Oracle scheduled job.

The job may start to run 3 days after the installation, and it runs daily at 6:15 AM. It checks the on-line message table, when the number of messages exceeds the 1.5 million threshold, it may move a half million of the messages into external table starting with older messages. Each external table contains a half million messages. The external tables may be created in dump file form in the subfolder called ExternalTables under a database or a data folder. The external table name may be in the form of "ET_DDMMYYYY_1", its dump file name may be in the form of "ET_DDMMYYYY_1.dmp".

Once the external table may be created, an entry may be added in the message tracking table for that table. When an error happens during this moving process, the Oracle error may be added into both the on-line message table and the message tracking table.

Clearing up email queue may happen automatically through a scheduled job called "CLEANUP_MAIL_SERVER_JOB". The job may start to run 3 days after the installation, and it runs daily at 6:00 AM. The job may delete any non-pending emails which may be older than 14 days.

After this first deletion, if the row count of the MAILSERVER database table exceeds 1000 entries, then the non-pending emails may be deleted, starting with the oldest emails by date, until the email count may be down no less than 1000.

The new message managing features may be incorporated into the existing Message Center Properties tool. It may be portable to put these features in one tool so that it may be utilized as a system level tool that the user may set up for all users if desired so.

Three new property pages may be implemented to manage messages. They may be Archive, Email Queue and Advanced as seen in the picture below. These tabs may be visible in this application. In the existing Message Board application, the General and Password tabs may also be visible in addition to these. The Purge tab may be removed.

This page may be designed to manage archiving of messages from the Online table. Messages may be exported immediately on demand. They may be exported automatically on schedule.

There may be two input entries that may be designated for the user to specify the archive interval of each message block. The smallest interval for a message block may be a day. The largest interval may be a year. This interval size also represents an archive unit. Messages may be preserved in the interval size chunks. It may be user's responsibility to set correct settings for their needs. The first text entry may be designed to accept a multiple of an archive interval type. The combo box next to it may be for the interval type, i.e. Any one of Day(s), Week(s), Month(s) or Year.

A combination of these two choices may determine the range of messages interval.

For example, if Day(s) may be chosen, the user has a choice of setting the number of days for the archive interval. The range may be from 1 to 6 days. The idea may be the same for the Week(s) choice. The range may be from 1 to 4 weeks. The range of the Month(s) choice may be from 1 to 11 months. Year range may be 1.

There may be another section for the size of messages that the user wants to retain in the Online table. The layout may be identical to that of the archive interval mentioned above. The user specifies the minimum volume of messages that the user wants to retain in the Online table. The rules for this section may be identical. The first text entry may be designed to accept a multiple of a retention interval type. The combo box next to it may be for the retention interval type, i.e. Any one of Day(s), Week(s), Month(s) or Year. A combination of these two choices may determine the range of messages interval.

In addition to these interval choices, there may be two scheduling choices, Archive Now and Schedule. The Archive Now button may be used independently of the Schedule choice. When the Archive Now button may be pressed, archiving starts right away and messages may be archived off of the Online table based on the interval choice. Messages may be archived based on the archive interval that may be set at the top of the page. This may be to keep the same archival unit to preserve messages.

If the interval time that may be chosen has not elapsed, the transfer may not happen. In such as case, a message may pop up saying "no messages may be ready to be exported" if no messages that match the interval. The same message may be written to the message board. In other word interval worth of messages may have not accumulated beyond the retention point, no archiving may occur.

The user may set the time to archive messages by filling both the Time and the AM/PM choices. The scheduled archive may occur the day after the requested archive interval elapsed. Even there may be no messages in the interval, there may be a dump file with no messages created.

Every time a block of messages may be exported from the Online table, a new Message Tracking Information Entry may be created. The Message Tracking Information Entry table shows the contents of the table. It has columns called Start Sequence and End Sequence. These values may be stored to the Message Tracking Information Entry table when each partition block may be created and shown in the table view. The sequence number combination gives the top/bottom limits of each partition.

The Active check box in the Message Tracking table indicate whether or not message blocks may be online or not.

All controls may be disabled while messages may be being archived.

The email queue properties page displays impending emails. The user may clear the email queue immediately by pressing the Clear Now button. All email requests may be deleted from the queue immediately. The check box right next it enables the user to clear pending emails also. This page also let the user schedule the clearance of requests on schedule.

The first text entry lets the user enter a multiple of clearance interval type. The combo box lets the user chose a clearance interval type. There may be 4 clearance types, day(s), week(s), Month(s) and Year.

A combination of these two choices may determine the range of messages interval.

For example, if Day(s) may be chosen, the user has a choice of setting the number of days for the archive interval. The range may be from 1 to 6 days. The idea may be the same for the Week(s) choice. The range may be from 1 to 4 weeks. The range of the Month(s) choice may be from 1 to 11 months. Year range may be 1.

This page shows the message tracking information entries that shows the current state of dump files/external tables. An external table may be created as each dump files may be generated. It may be always online. The external file must exist once it is created. The Online check box indicates if an external table may be readily available for viewing or not. If it may be turned off, it means the particular external table may be not available for some reasons. It could may have been deleted. The dump file that may be associated with the external file could be missing.

Pressing the Update button may reestablish the external table and refresh the message tracking information table. The external table may be recreated if necessary. Once the external table may be back on line, the Active check box may be turned on. A message may be put up if the dump file may be missing even after the table may be updated.

If a job may be pending, it may be identified by a flag, Being Archived. If it may be on, it means that indicates it has started, but it has not been finished. A message may be put up in such a case.

In such a case, the user has two choices. One choice may be to initiate the same job right away using the same archiving condition by pressing the Retry Archive button. When the new job may be finished without an issue, the message tracking information entry may be updated accordingly.

Another choice may be to exclude the message tracking information entry and skip it. The entry may be there, but it may not be used. The user may then go back to the Archive page to perform archiving right away or schedule a new job. The user may use a different archiving interval.

The E-Mail system policy page may be updated to incorporate text messaging. A new column called "Send Text(s) To" may be added to allow the user to set up a text message address.

The message may be delivered to these addressed at the same time if both may be specified.

There may be a new e-mail type called Immediate. Users who subscribe to such messages may receive notifications when messages, that require immediate attention, may be issued.

There may be a few more columns added to the table so that user may have granularity to choose messages to that they want to subscribe. (We may have not determined what they may be yet.)

Figure 8A:
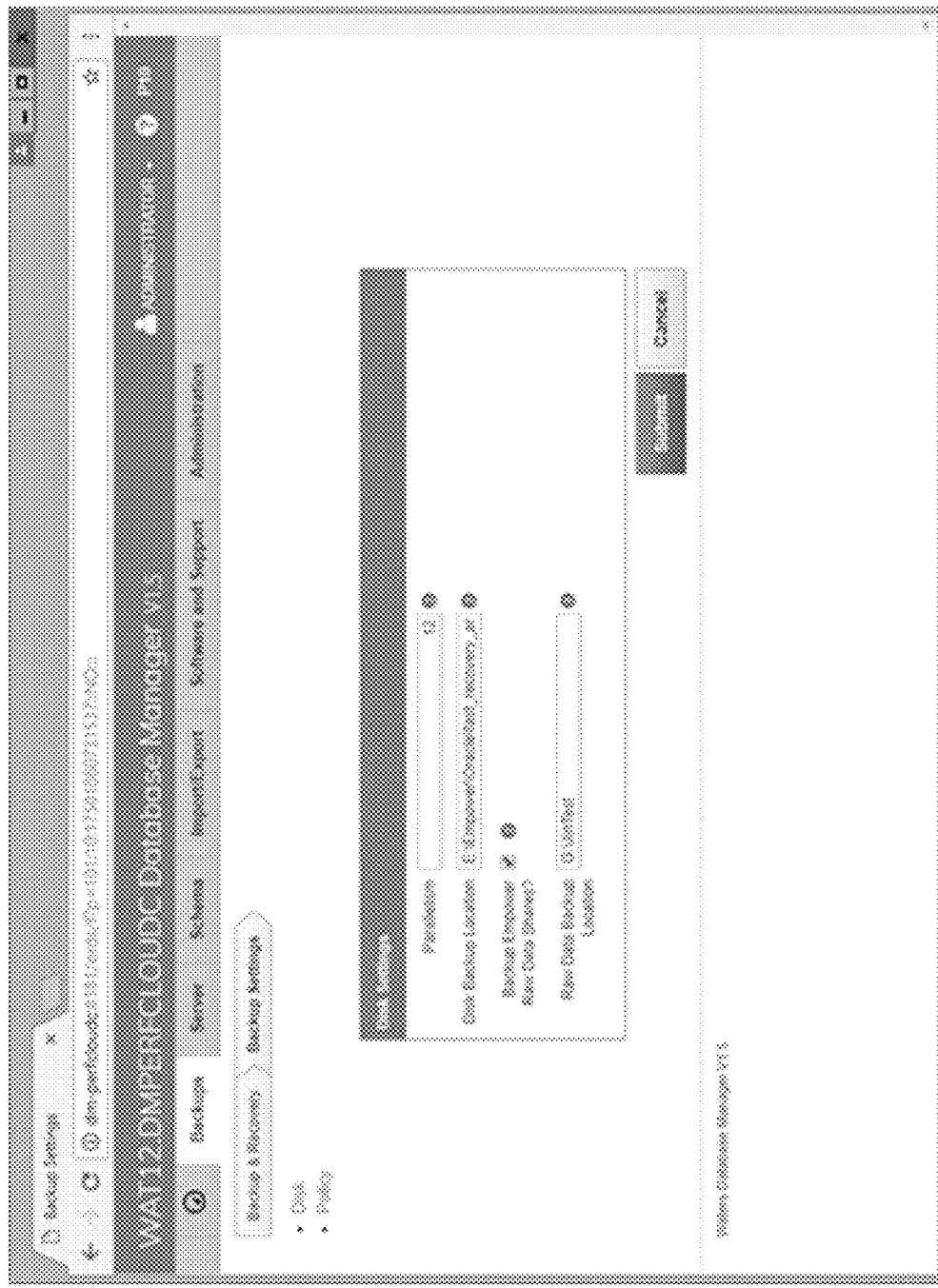
FIGS. 8A-8C illustrate exemplary aspects of archiving/retrieving online/offline messages according to one or more embodiments described herein.
Figure 8B:
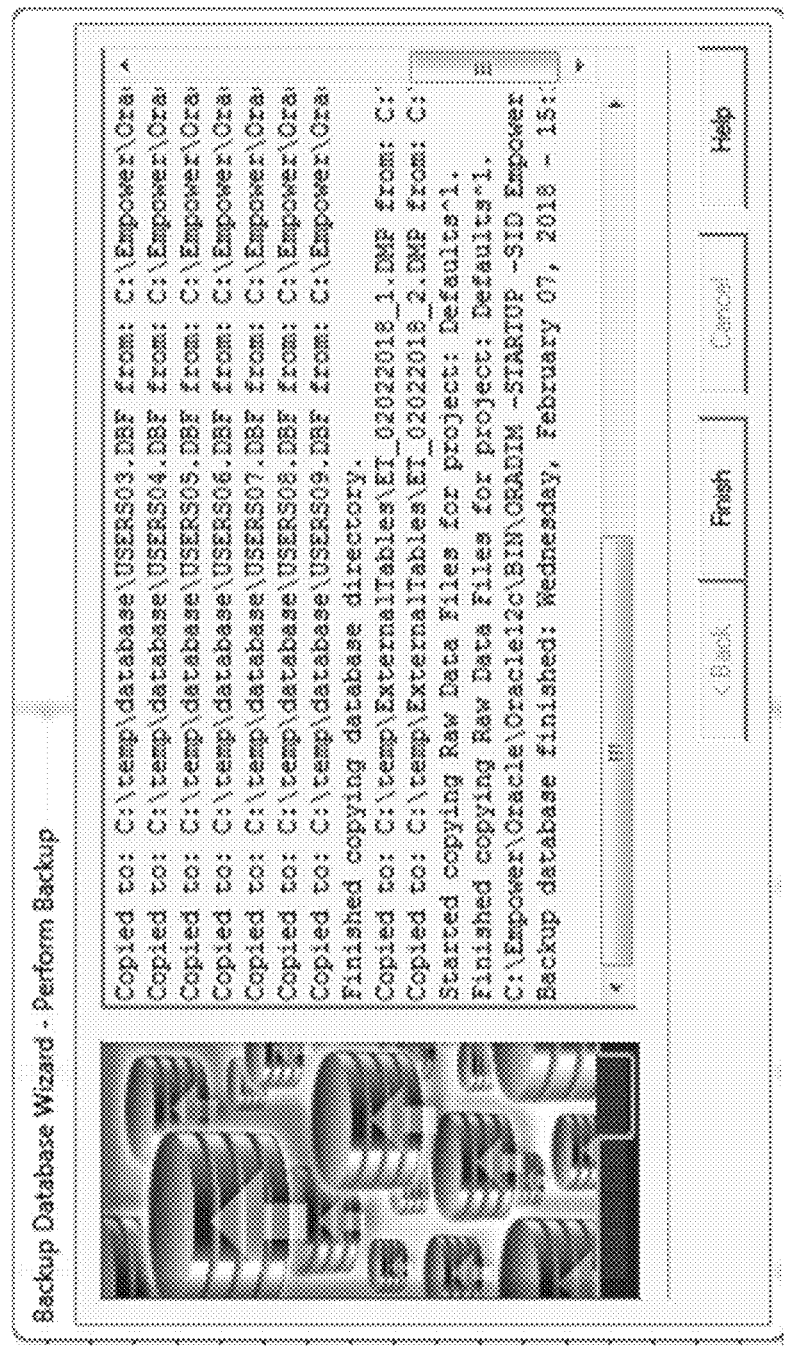
Figure 8C:
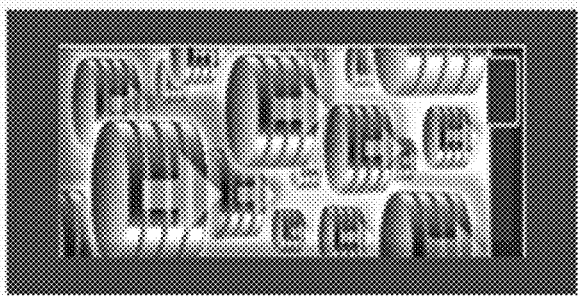

FIGS. 8A-8C illustrate exemplary aspects of archiving online messages or retrieving offline messages according to one or more embodiments described herein. In various embodiments, archiving/retrieving of online/offline messages may be implemented by one or more portions of message controller 104. For instance, archiving online messages may be implemented by message manager 220 and retrieval of offline messages may be implemented by message viewer 222. Embodiments are not limited in this context.

To enable WDM to back up the external tables, the option of "Backup Raw Data Share" must be turned on. The backup files may be located in a subfolder under the "Raw Data Backup Location" setting, called external tables, for example, if the "Raw Data Backup Location" may be set to "G:\RawData", then the external tables may be backed up to "G:\RawData\externaltables".

To restore the backup, run the backupscript\recover_DF.BAT file under the same "Raw Data Backup Location".

For database backup on a workstation, once the destination directory path may be entered and the Next button may be clicked, if the sub-directory "ExternalTables" does not exist, it may be created. While the directory may be being created, if the destination path may be longer than 248 characters, the existing path too long error message may popup. If another error happens, the existing error message "Could not create the backup subdirectory" may pop up.

If the sub-directory "ExternalTables" does exist, the backup process may make sure that it's empty; if not, the existing backup directory not empty error message may pop up.

Once the backup process starts copying the files, if the backup succeeds, the copy to message may be added to the rolling text field and backup log file; if the backup fails, existing error message may be added into the backup log file.

Note that, during the backup process, the external tables may be always copied after the regular database files and before the raw data files as shown in FIG. 8B.

For a database restore on a workstation, once the source directory path may be entered, and the Next button may be clicked, if the sub-directory "ExternalTables" does not exist, a new error message may popup, stating "Cannot restore message center external tables because the ExternalTables folder cannot be found in the specified directory. Continue restoring the database?" When the OK button is clicked, the restore process may continue, when the NO button is clicked, the process may stop.

When the restore process starts copying the external table files, if there may be an empty ExternalTables source directory, no message may be displayed. If the source ExternalTables directory may be missing, the following error message may be added to the restore log:

"Cannot restore message center external tables because the ExternalTables directory cannot be found in the specified directory. Copy the message center external tables manually."

If the destination directory for the external tables already exists, all files in it should be removed, if error happens during this cleanup, the following error message may be added to the restore log:

"No message center external tables were restored because the files contained in the directory: <directoryname> could not be removed."

If the destination directory for the external tables does not exist, it may be created. While the directory may be being created, if error happens, the following error message may be added to the restore log:

"No message center external tables were restored because the directory: <directoryname> was not created."

If the destination drive for the external tables does not may have enough space, the following error message may be added to the restore log:

"Cannot restore message center external tables because the directory: <directoryname> does not contain enough free space. The message center external tables must be copied manually."

Note that in various embodiments, during the restore process, the external tables may be restored after the regular database files and before the raw data files as shown in FIG. 8C. Note also that in many embodiments for backup and/or restore processes, the whole source directory and/or all files may be copied. Therefore, any additional non-related files in the source directory may be also copied with the usual database files.

Figure 9A:
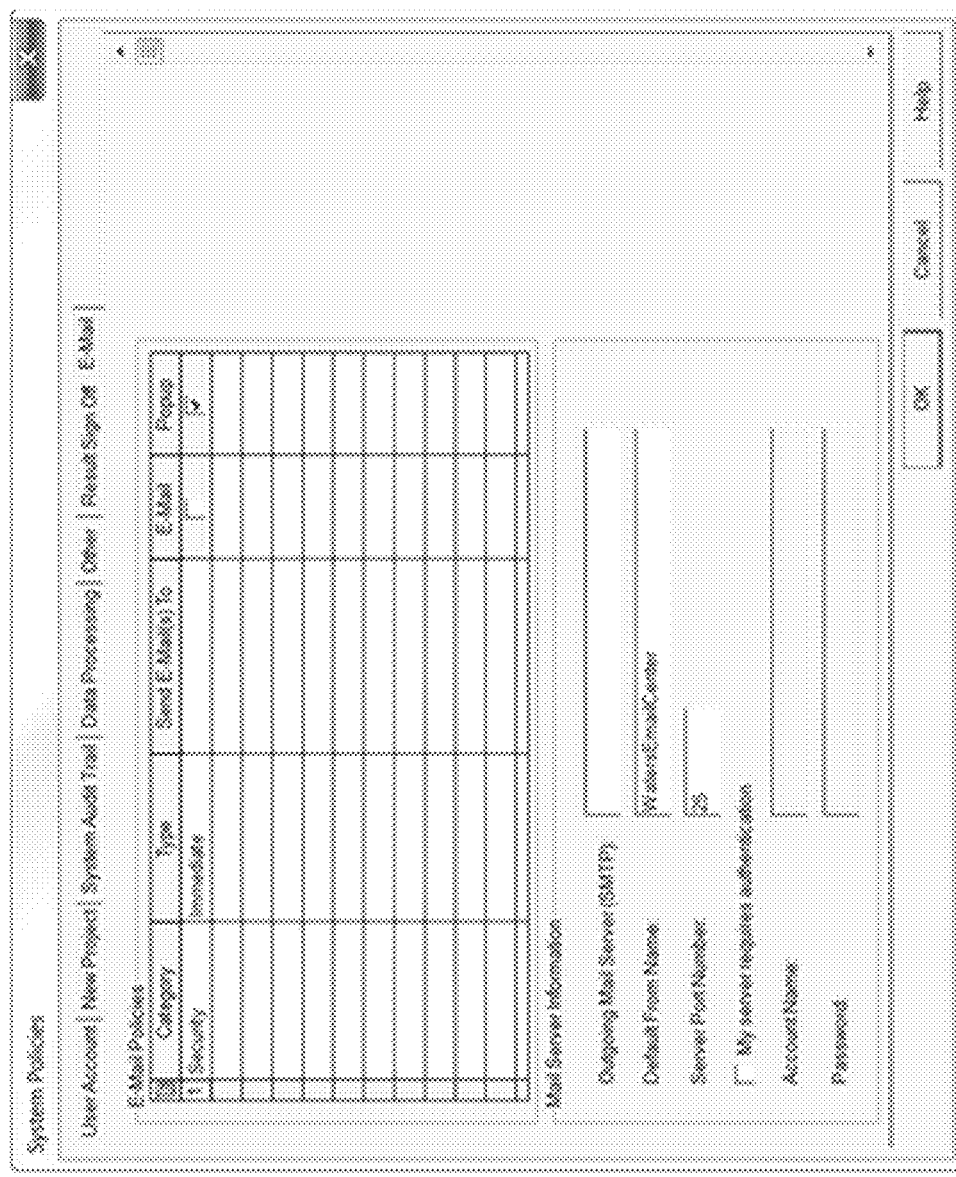
FIGS. 9A-9C illustrate exemplary aspects of immediate attention message properties according to one or more embodiments described herein.
Figure 9B:
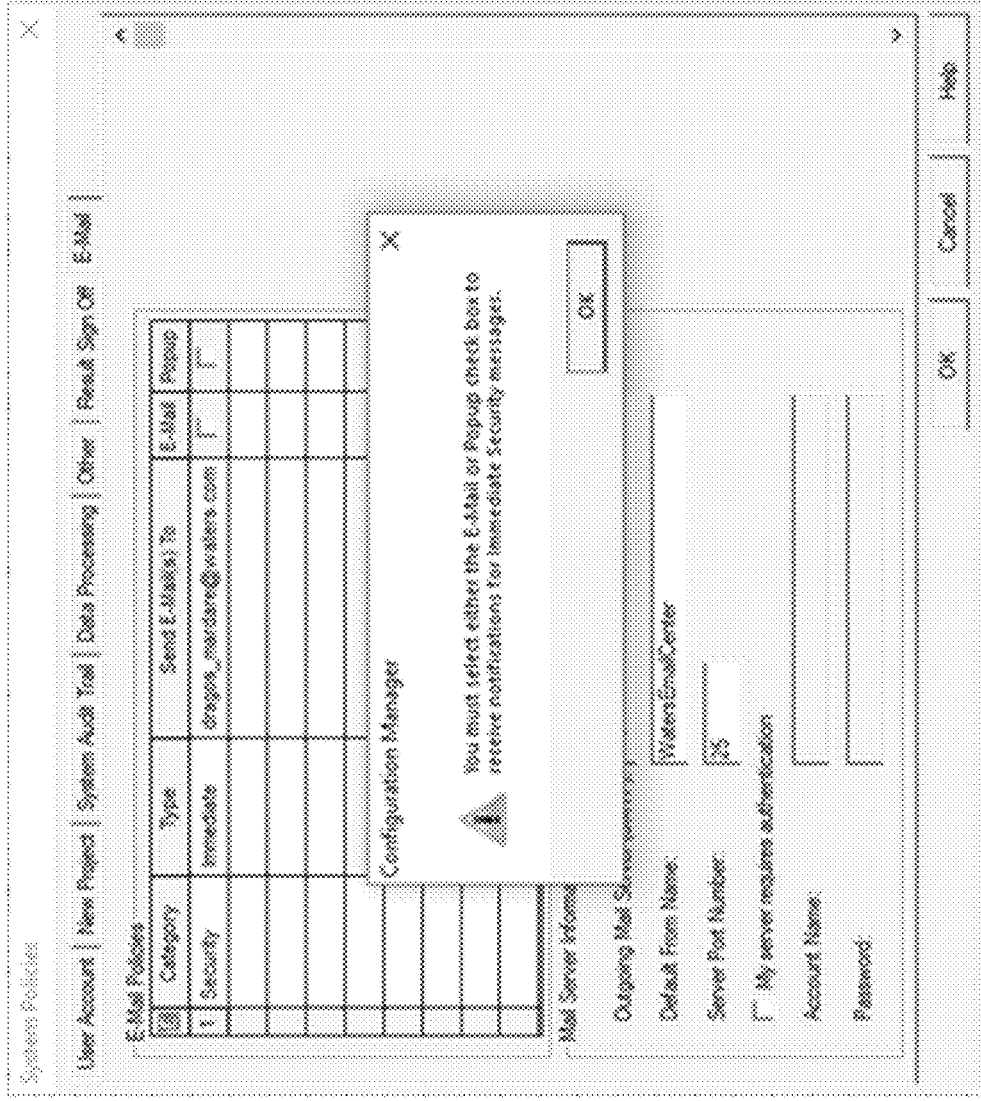
Figure 9C:
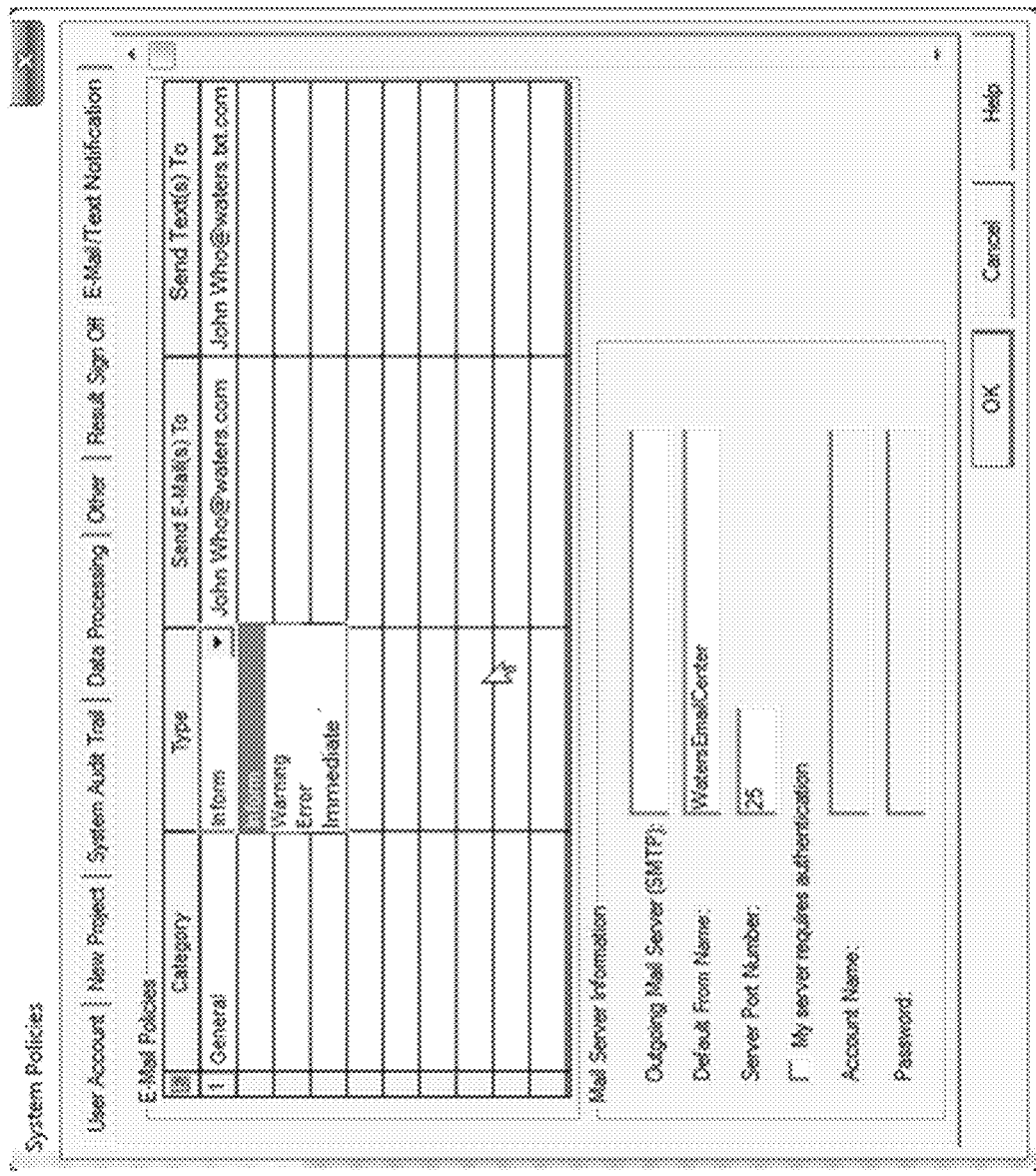

FIGS. 9A-9C illustrate exemplary aspects of immediate attention message properties according to one or more embodiments described herein. In various embodiments, the immediate attention message properties may be associated with user defined settings of message controller 104, such as rules for the generation and/or communication of immediate attention messages 114. Embodiments are not limited in this context.

In several embodiments, there may be a mechanism for Immediate attention message delivery using the E-Mail Service. In some embodiments, this may be set from the E-Mail tab of the System Policies dialog box. In various embodiments, the first row of the E-Mail Policies table may be set to Category=Security and Type=Immediate, with the popup box checked, and E-Mail box unchecked. In various such embodiments, this may occur by default. In one or more embodiments, the first row cannot be deleted. In some embodiments, when neither checkbox is checked, an error message may be displayed stating that at least one mechanism must be selected.

If the E-Mail checkbox may be checked, the E-Mail address box may not be empty. If the box may be empty, an error message may be displayed stating that at least one E-Mail address must be supplied. Both checkboxes may also be checked at the same time, if the E-Mail address box may be not empty. Whenever an E-Mail policy has been set that requires an E-Mail address, and the Outgoing Mail Server (SMTP) may be not specified, then a message may be displayed stating that it may be required. The new checkboxes for the notification mechanism may be only alterable in row 1 of the table. The checkboxes may be unalterable in every other row and may be set to checked for E-Mail and unchecked for Popup.

If the popup box may be checked, all users with the privilege "Administrator" may see a popup box for Immediate messages. The message may show in 30 seconds or less if an administrator may be currently logged in, otherwise it may be shown when an administrator logs in and opens a Message Center application. If the popup box may be checked, and an Immediate message may be generated while an administrator may be logged in, but while no Message Center application may be running, then the popup message may not be presented until one may be opened. If the popup box may be not checked, no users may see a popup box for the Immediate type message. Only unsuccessful login attempts may be considered a message of type Immediate.

In some embodiments, administrators may see only one popup message regardless of how many Immediate attention messages may be present until the message may be closed. When the OK button on the message may be pressed, the message may close and Message Center may automatically open to the All Messages tab. If an Administrator user may be currently logged in, and there may be already at least one pending Immediate attention message and another one may be generated, then the existing popup message may be replaced with a new one.

Figure 10:
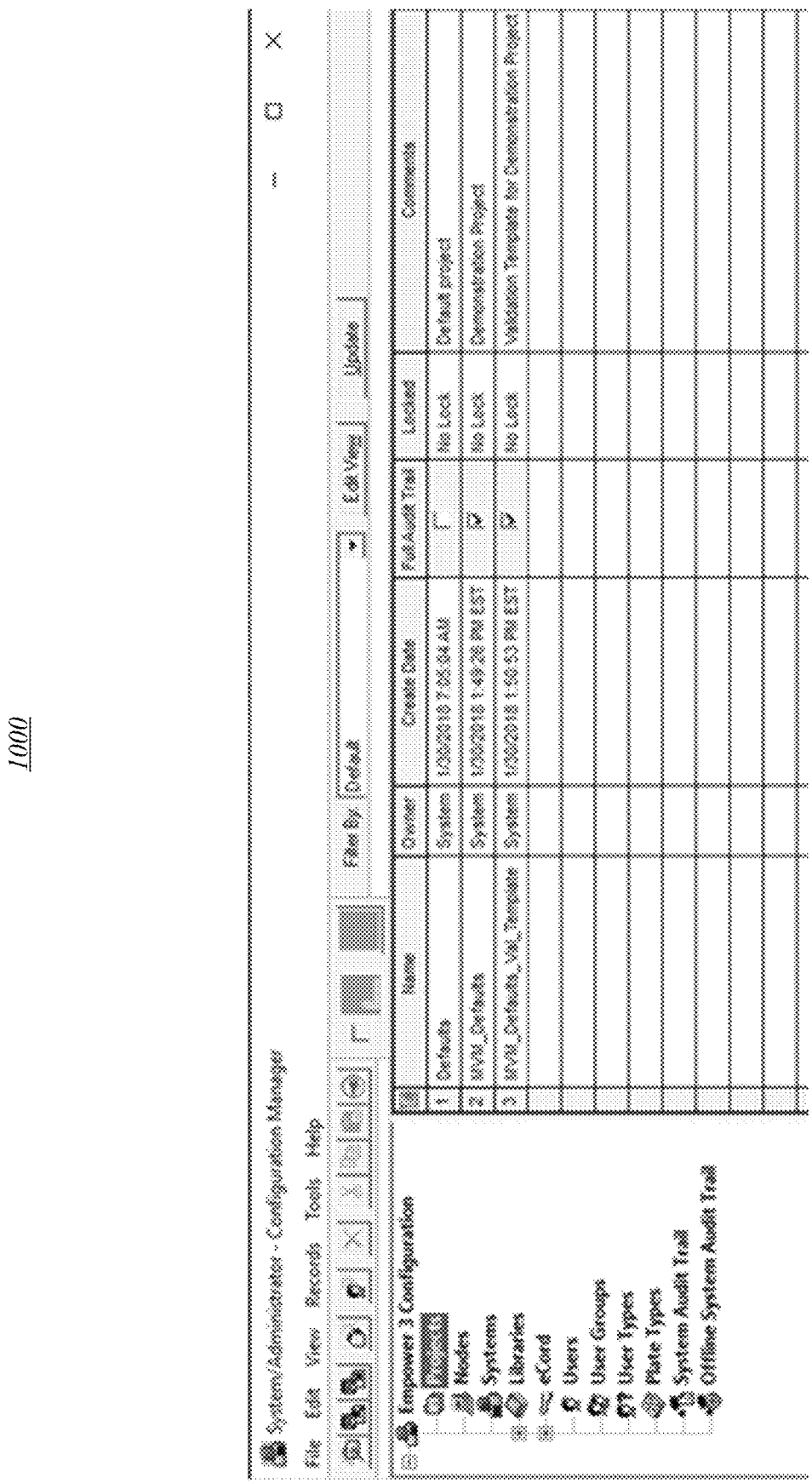
FIG. 10 illustrates exemplary aspects of message center error notification according to one or more embodiments described herein.

FIG. 10 illustrates exemplary aspects of message center error notification according to one or more embodiments described herein. In various embodiments, the message center error notifications may be implemented by one or more portions of message controller 104. For instance, message manager 220 may implement message venter error notifications based on user defined rules. Embodiments are not limited in this context.

Whenever the current user has an unread error type message in Message Center, the Message Center icon implemented in the applications that may be owned by this user may change color to red and the tooltip for this button may change to display the error count (this may apply for all instances owned by the current users no matter the user type or terminal used to login). The Message Center icon in applications owned by other users may not change color due to the current user errors, except for Administrators users which may be getting notifications for all errors.

Message Center does error message polling for current user every 30 seconds. When an unread error message may be detected, Message Center may broadcast a signal to all applications in the same interval. Each application may check the notification and determine if the Message Center button needs to change color to red or to be reset to its normal state and may change the color of the button accordingly.

The Message Center button may reset to its normal state when all unread error messages may have been read. Messages may be noted as being read when the user opens Message Center to the My Messages view, or, if the Message Center may be already open to the My Messages view, by clicking update. Reading the error messages as Administrator may not clear the notification for any other user. Although all user types of the same user may get notifications for all errors created with all user types, reading the error messages with one user type may not clear the notification for all of them.

When unread error type messages may be present in Message Center, the Message Center button's tooltip in all applications including the Message Center may show "Error Count (x)", where x=number of unread error messages for the currently logged in user. When there may be no unread error messages, then the tooltip goes back to "Message Center" or, in the Message Center application, "Show Latest Messages".

In any non-Message Center application, when the user presses the Message Center button either green or red, Message Center may be open/brought in front with the 'My Messages' view on top (or, if Administrator user type, the 'All Messages' view), and that view may be updated automatically thus showing the most recent messages. If the button was red, then the tooltip on the Message Center button in all applications may change to "Message Center" (or "Show Latest Messages" in the Message Center app) instead of a number and the color of all "Message Center" buttons may return to the default color.

Figure 11A:
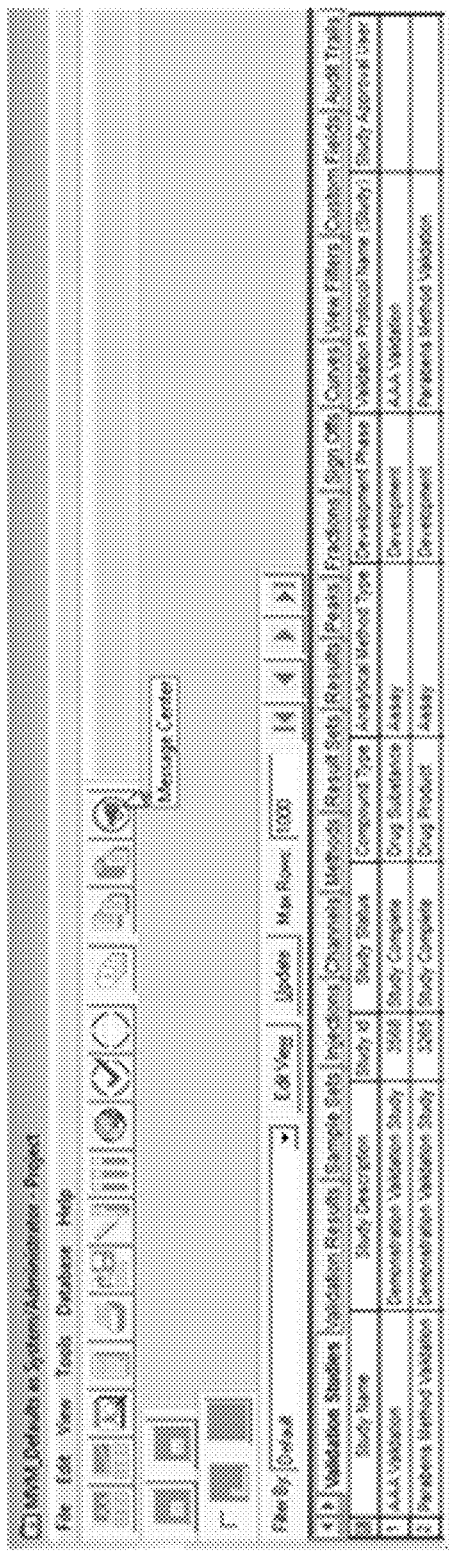
FIGS. 11A and 11B illustrate exemplary aspects of message center access according to one or more embodiments described herein.
Figure 11B:
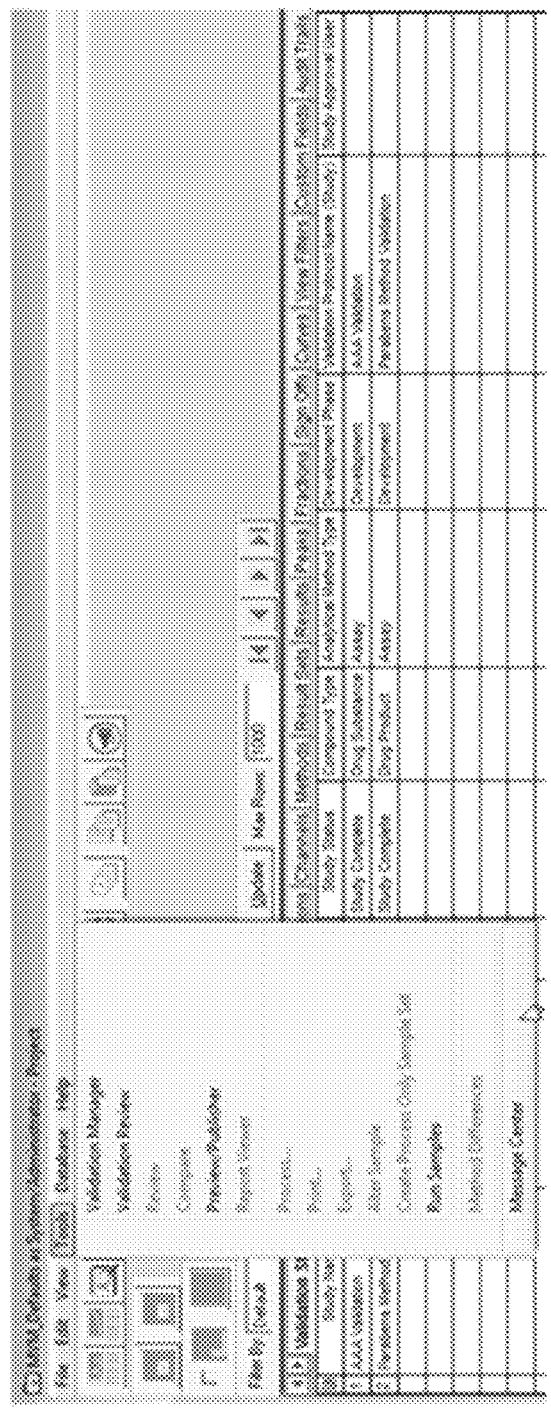

FIGS. 11A and 11B illustrate exemplary aspects of message center access according to one or more embodiments described herein. In various embodiments, access to message center 104 (e.g., a GUI for interacting therewith) may be possible from numerous different devices and/or applications. Embodiments are not limited in this context.

A toolbar icon and a menu item called Message Center were added to the following applications: Configuration Manager, Project Window, Review, Run Samples, Validation Review, Validation Manager, Quickstart, Compare, Report Publisher, Walk Up (Menu item only).

The Message Center menu item may be found under Tools in every application listed above and the new icon may have a tooltip that indicates "Message Center".

In the Walk-Up interface, there may be a menu item "Message Center" under the View menu; there may be no message center icon.

The Message Center process may be started and seen in Task Manager when any of the applications listed above may be launched. Each user/usertype may have its own Message Center process. The Message Center process for a specific user/usertype may close when all applications listed above for that user/usertype may be closed.

Selecting either the icon or the menu item may launch Message Center if it may be not already running and bring it to front. If using an Administrator user type, it may update the "All Messages" view. Otherwise, it may update the "My Messages" view. The views may update whether the button was initially the default color or red.

When a user/user type closes the Message Center window, the Message Center continues to run as a background process as long as that user/user type has other applications open. When this happens, there may be no Message Center application icon in the taskbar and no system tray icon. Selecting the new Message Center icon from any open application may reopen the window, show in the taskbar as an open application, and update the message views as described above. When the last application associated with a user/user type may be closed, then the Message Center background process may be closed as well. At least one application may be required to be open in order to view Message Center.

In many embodiments, when a new project is created or a project is cloned and "Perform Shallow Copy of Methods" is utilized in the project audit trail, the "Shallow Copied Methods" action may be recorded instead of the "Copied Method" action. In some embodiments, in the System Audit Trail the "Created Project using shallow copy"/"Cloned Project using shallow copy" action may be recorded instead of "Created project"/"Cloned Project" action when methods are copied using shallow copy during project creation.

In several embodiments, a project integrity test may be added at the beginning of project backup. In several such embodiments, there may be two integrity tests during backup of a project. The first integrity test may occur before backup, on the project stored in the database and in the file share. The results of the first integrity check may be stored in the database as part of the project. The second integrity test may occur after the backup is complete, on the backed-up project directory (not in the database). The results of the second integrity check may be stored in the project's backup directory with the rest of the backed-up project.

During project backup, the following occurs due to the integrity tests:

An entry may be made in the System Audit Trail for each of the integrity tests, indicating whether it was an integrity test on the project or on the produced project backup, and whether the integrity test succeeded or failed.

The result of the first integrity test may be recorded in the project properties' integrity tab.

The result of the second integrity test may be in the file Project Integrity.txt, stored with the produced project backup, and may be not recorded in the project properties' integrity tab.

When either integrity test fails, appropriate message(s) may be sent to the message center indicating whether it was an integrity test on the project or on the produced project backup.

During backup of a single project, if the first integrity test fails, a popup may be seen indicating that the integrity test failed on the project, and the user has the choice to continue the backup or not; if the second integrity test fails, a popup may be seen indicating that the integrity test failed on the produced project backup, and the user may only choose "OK" from that message.

No popups about integrity failures may be seen during backup of multiple projects.

During batch backup, a batch backup timestamped log file may be saved at the \Logs directory showing the result (succeeded or failed) of both types of integrity tests on each backed-up project.

Figure 12A:
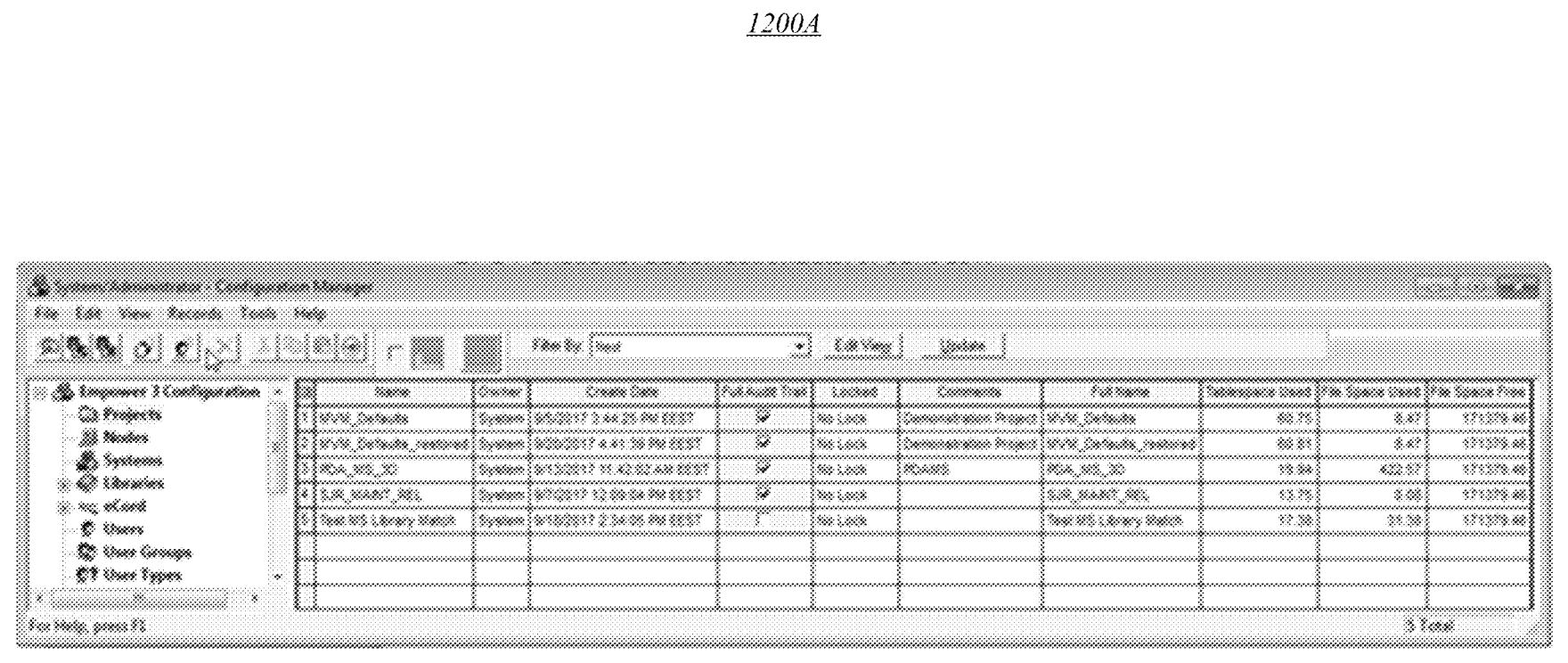
Figure 12B:
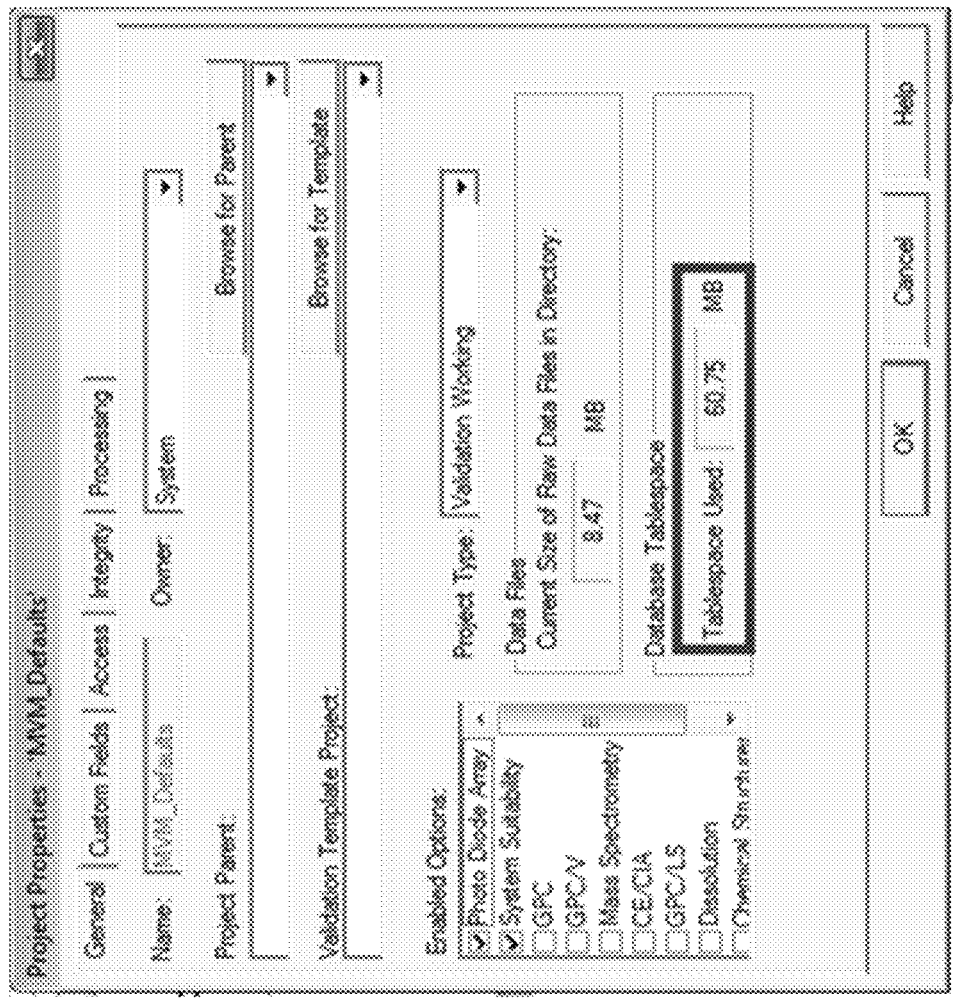
Figure 12C:
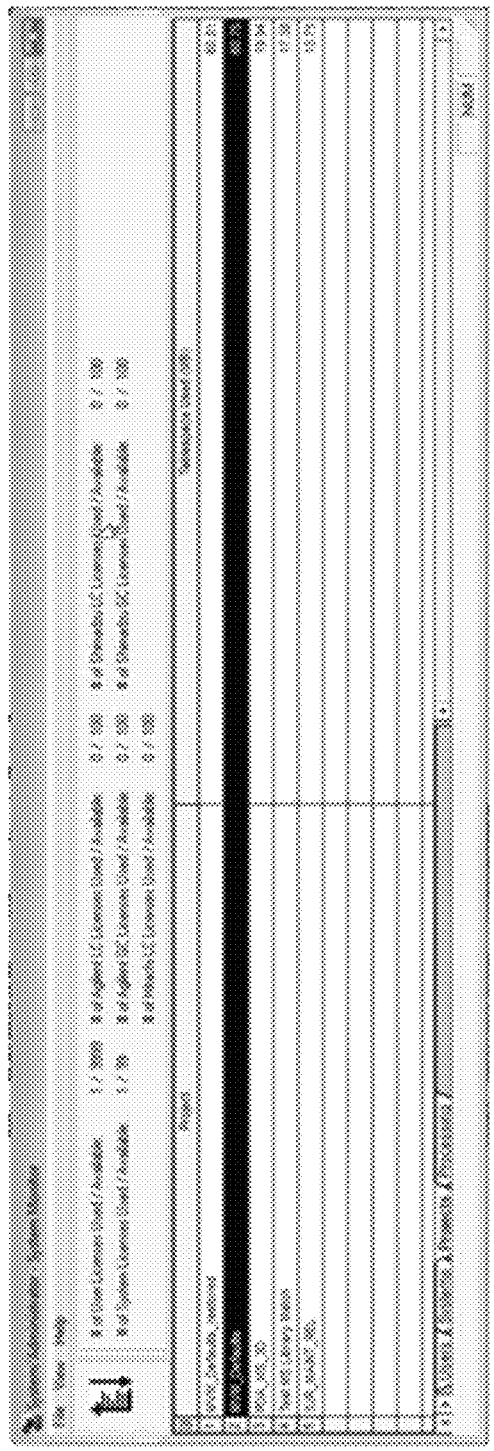

FIGS. 12A-12C illustrate exemplary aspects of table space usage according to one or more embodiments described herein. In various embodiments, message controller 104 may track table space usage associated with one or more of online messages 108 and offline messages 112, such as via message manager 220. Embodiments are not limited in this context.

In some embodiments, projects may have unlimited quota. In other embodiments, projects may have limited quota. In such other embodiments, quota checks may be used. In embodiments with unlimited quota, one or more of the following UI changes may be utilized when compared to embodiments with limited quota: Configuration Manager— Tablespace Quota and Tablespace Free columns removed from project table view. A new column, Tablespace Used, may be added that displays the amount of database tablespace used in MB for each project. System Monitor— "TableSpace Free (MB)" and "TableSpace Quota (MB)" may be removed. A new column may be added, "TableSpace Used (MB)", which may display the amount of database tablespace used in MB for each project.

Figure 13:
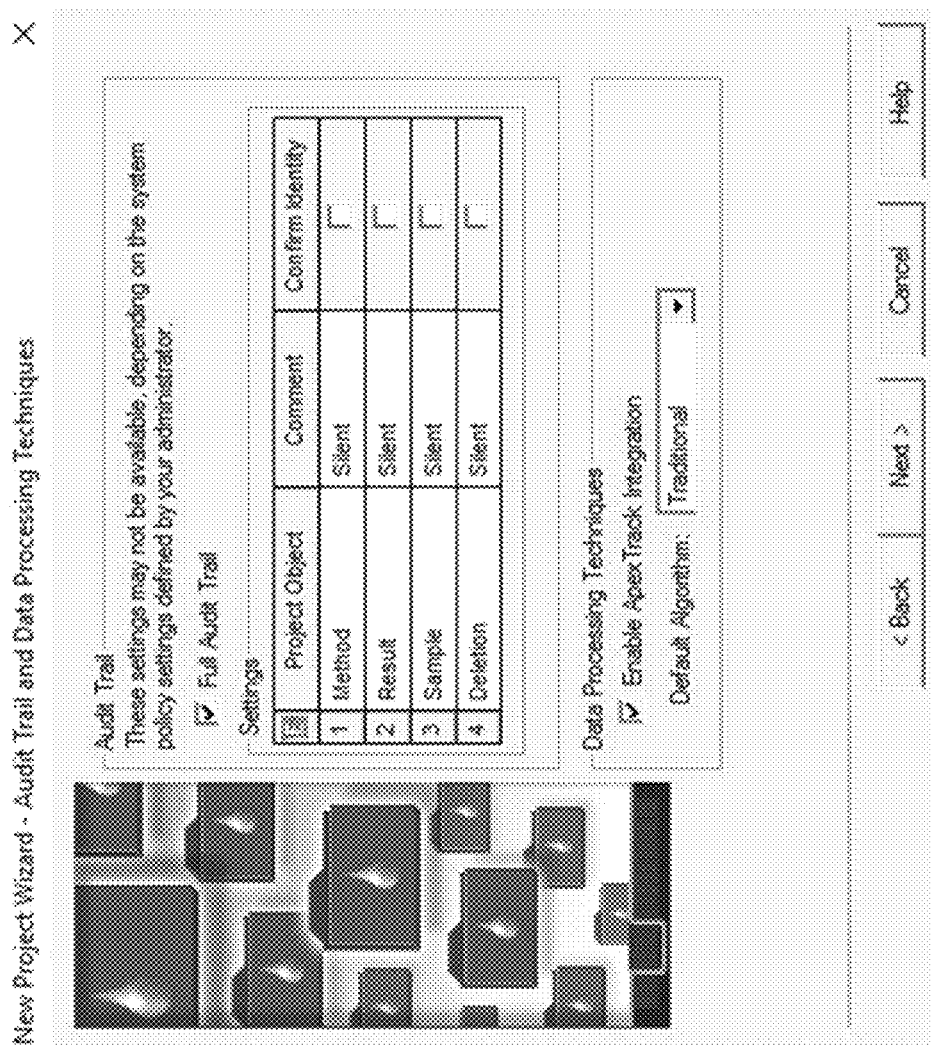
FIG. 13 illustrates exemplary aspects of an audit trail according to one or more embodiments described herein.

FIG. 13 illustrates exemplary aspects of an audit trail according to one or more embodiment described herein. In various embodiments, an audit trail may be generated by message controller 104, such as for regulatory or tracking purposes (e.g., block chain). Embodiments are not limited in this context.

In some embodiments, when an injection/channel/sample set/result set is deleted, any associated items that are deleted automatically may appear in the Audit Trail. Also, or alternatively, when a result or a result set is deleted a message may appear stating all the associated items that may also be deleted.

FIG. 14 illustrates an embodiment of a storage medium 1400. Storage medium 1400 may comprise any non-transitory computer-readable storage medium or machine-readable storage medium, such as an optical, magnetic or semiconductor storage medium. In various embodiments, storage medium 1400 may comprise an article of manufacture. In some embodiments, storage medium 1400 may store computer-executable instructions, such as computer-executable instructions to implement one or more of logic flows or operations described herein. Examples of a computer-readable storage medium or machine-readable storage medium may include any tangible media capable of storing electronic data, including volatile memory or non-volatile memory, removable or non-removable memory, erasable or non-erasable memory, writeable or re-writeable memory, and so forth. Examples of computer-executable instructions may include any suitable type of code, such as source code, compiled code, interpreted code, executable code, static code, dynamic code, object-oriented code, visual code, and the like. The embodiments are not limited in this context.

Figure 15:
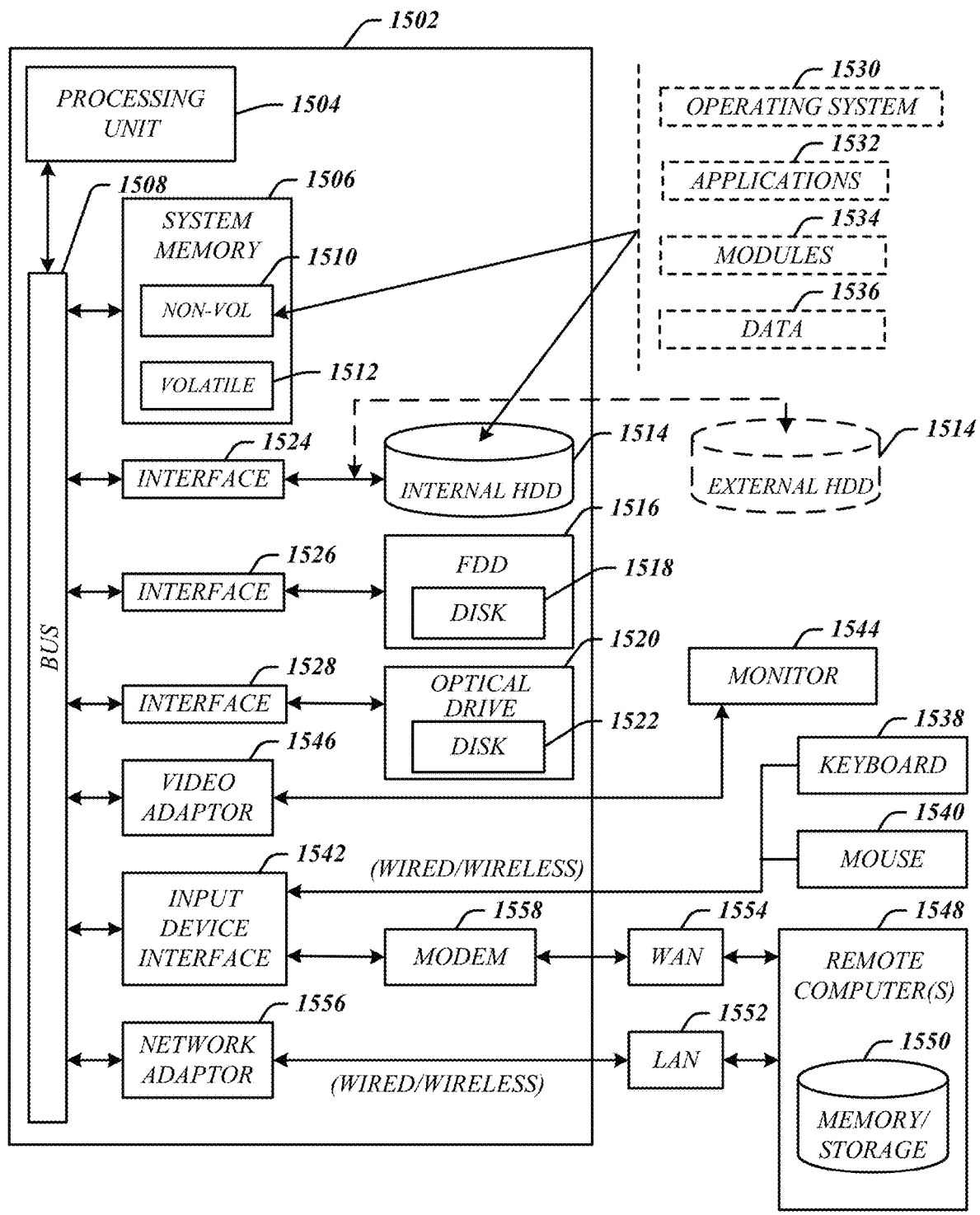
FIG. 15 illustrates an embodiment of a computing architecture according to one or more embodiments described herein.

FIG. 15 illustrates an embodiment of an exemplary computing architecture 1500 that may be suitable for implementing various embodiments as previously described. In various embodiments, the computing architecture 1500 may comprise or be implemented as part of an electronic device. In some embodiments, the computing architecture 1500 may be representative, for example, of a distributed processing system that implements or utilizes one or more components described herein. In some embodiments, computing architecture 1500 may be representative, for example, of a compute node in a distributed processing system described herein that implements or utilizes one or more techniques described herein. The embodiments are not limited in this context.

As used in this application, the terms "system" and "component" and "module" may be intended to refer to a computer-related entity, either hardware, a combination of hardware and software, software, or software in execution, examples of which may be provided by the exemplary computing architecture 1500. For example, a component may be, but may be not limited to being, a process running on a processor, a processor, a hard disk drive, multiple storage drives (of optical and/or magnetic storage medium), an object, an executable, a thread of execution, a program, and/or a computer. By way of illustration, both an application running on a server and the server may be a component. One or more components may reside within a process and/or thread of execution, and a component may be localized on one computer and/or distributed between two or more computers. Further, components may be communicatively coupled to each other by various types of communications media to coordinate operations. The coordination may involve the uni-directional or bi-directional exchange of information. For instance, the components may communicate information in the form of signals communicated over the communications media. The information may be implemented as signals allocated to various signal lines. In such allocations, each message may be a signal. Further embodiments, however, may alternatively employ data messages. Such data messages may be sent across various connections. Exemplary connections include parallel interfaces, serial interfaces, and bus interfaces.

The computing architecture 1500 includes various common computing elements, such as one or more processors, multi-core processors, co-processors, memory units, chipsets, controllers, peripherals, interfaces, oscillators, timing devices, video cards, audio cards, multimedia input/output (I/O) components, power supplies, and so forth. The embodiments, however, may be not limited to implementation by the computing architecture 1500.

As shown in FIG. 15, the computing architecture 1500 comprises a processing unit 1504, a system memory 1506 and a system bus 1508. The processing unit 1504 may be any of various commercially available processors, including without limitation an AMD® Athlon®, Duron® and Opteron® processors; ARM® application, embedded and secure processors; IBM® and Motorola® DragonBall® and PowerPC® processors; IBM and Sony® Cell processors; Intel® Celeron®, Core (2) Duo®, Itanium®, Pentium®, Xeon®, and XScale® processors; and similar processors. Dual microprocessors, multi-core processors, and other multi-processor architectures may also be employed as the processing unit 1504.

The system bus 1508 provides an interface for system components including, but not limited to, the system memory 1506 to the processing unit 1504. The system bus 1508 may be any of several types of bus structure that may further interconnect to a memory bus (with or without a memory controller), a peripheral bus, and a local bus using any of a variety of commercially available bus architectures. Interface adapters may connect to the system bus 1508 via a slot architecture. Example slot architectures may include without limitation Accelerated Graphics Port (AGP), Card Bus, (Extended) Industry Standard Architecture ((E)ISA), Micro Channel Architecture (MCA), NuBus, Peripheral Component Interconnect (Extended) (PCI(X)), PCI Express, Personal Computer Memory Card International Association (PCMCIA), and the like.

The system memory 1506 may include various types of computer-readable storage media in the form of one or more higher speed memory units, such as read-only memory (ROM), random-access memory (RAM), dynamic RAM (DRAM), Double-Data-Rate DRAM (DDRAM), synchronous DRAM (SDRAM), static RAM (SRAM), programmable ROM (PROM), erasable programmable ROM (EPROM), electrically erasable programmable ROM (EEPROM), flash memory (e.g., one or more flash arrays), polymer memory such as ferroelectric polymer memory, ovonic memory, phase change or ferroelectric memory, silicon-oxide-nitride-oxide-silicon (SONOS) memory, magnetic or optical cards, an array of devices such as Redundant Array of Independent Disks (RAID) drives, solid state memory devices (e.g., USB memory, solid state drives (SSD) and any other type of storage media suitable for storing information. In the illustrated embodiment shown in FIG. 15, the system memory 1506 may include non-volatile memory 1510 and/or volatile memory 1512. In some embodiments, system memory 1506 may include main memory. A basic input/output system (BIOS) may be stored in the non-volatile memory 1510.

The computer 1502 may include various types of computer-readable storage media in the form of one or more lower speed memory units, including an internal (or external) hard disk drive (HDD) 1514, a magnetic floppy disk drive (FDD) 1516 to read from or write to a removable magnetic disk 1518, and an optical disk drive 1520 to read from or write to a removable optical disk 1522 (e.g., a CD-ROM or DVD). The HDD 1514, FDD 1516 and optical disk drive 1520 may be connected to the system bus 1508 by a HDD interface 1524, an FDD interface 1526 and an optical drive interface 1528, respectively. The HDD interface 1524 for external drive implementations may include at least one or both of Universal Serial Bus (USB) and Institute of Electrical and Electronics Engineers (IEEE) 994 interface technologies. In various embodiments, these types of memory may not be included in main memory or system memory.

The drives and associated computer-readable media provide volatile and/or nonvolatile storage of data, data structures, computer-executable instructions, and so forth. For example, a number of program modules may be stored in the drives and memory units 1510, 1512, including an operating system 1530, one or more application programs 1532, other program modules 1534, and program data 1536. In one embodiment, the one or more application programs 1532, other program modules 1534, and program data 1536 may include, for example, the various applications and/or components of message controller 104.

A user may enter commands and information into the computer 1502 through one or more wire/wireless input devices, for example, a keyboard 1538 and a pointing device, such as a mouse 1540. Other input devices may include microphones, infra-red (IR) remote controls, radio-frequency (RF) remote controls, game pads, stylus pens, card readers, dongles, finger print readers, gloves, graphics tablets, joysticks, keyboards, retina readers, touch screens (e.g., capacitive, resistive, etc.), trackballs, trackpads, sensors, styluses, and the like. These and other input devices may be often connected to the processing unit 1504 through an input device interface 1542 that may be coupled to the system bus 1508, but may be connected by other interfaces such as a parallel port, IEEE 994 serial port, a game port, a USB port, an IR interface, and so forth.

A monitor 1544 or other type of display device may be also connected to the system bus 1508 via an interface, such as a video adaptor 1546. The monitor 1544 may be internal or external to the computer 1502. In addition to the monitor 1544, a computer typically includes other peripheral output devices, such as speakers, printers, and so forth.

The computer 1502 may operate in a networked environment using logical connections via wire and/or wireless communications to one or more remote computers, such as a remote computer 1548. In various embodiments, one or more migrations may occur via the networked environment. The remote computer 1548 may be a workstation, a server computer, a router, a personal computer, portable computer, microprocessor-based entertainment appliance, a peer device or other common network node, and typically includes many or all of the elements described relative to the computer 1502, although, for purposes of brevity, only a memory/storage device 1550 may be illustrated. The logical connections depicted include wire/wireless connectivity to a local area network (LAN) 1552 and/or larger networks, for example, a wide area network (WAN) 1554. Such LAN and WAN networking environments may be commonplace in offices and companies, and facilitate enterprise-wide computer networks, such as intranets, all of which may connect to a global communications network, for example, the Internet.

When used in a LAN networking environment, the computer 1502 may be connected to the LAN 1552 through a wire and/or wireless communication network interface or adaptor 1556. The adaptor 1556 may facilitate wire and/or wireless communications to the LAN 1552, which may also include a wireless access point disposed thereon for communicating with the wireless functionality of the adaptor 1556.

When used in a WAN networking environment, the computer 1502 may include a modem 1558, or may be connected to a communications server on the WAN 1554, or has other means for establishing communications over the WAN 1554, such as by way of the Internet. The modem 1558, which may be internal or external and a wire and/or wireless device, connects to the system bus 1508 via the input device interface 1542. In a networked environment, program modules depicted relative to the computer 1502, or portions thereof, may be stored in the remote memory/storage device 1550. It may be appreciated that the network connections shown may be exemplary and other means of establishing a communications link between the computers may be used.

The computer 1502 may be operable to communicate with wire and wireless devices or entities using the IEEE 802 family of standards, such as wireless devices operatively disposed in wireless communication (e.g., IEEE 802.16 over-the-air modulation techniques). This includes at least Wi-Fi (or Wireless Fidelity), WiMax, and Bluetooth™ wireless technologies, among others. Thus, the communication may be a predefined structure as with a conventional network or simply an ad hoc communication between at least two devices. Wi-Fi networks use radio technologies called IEEE 802.11x (a, b, g, n, etc.) to provide secure, reliable, fast wireless connectivity. A Wi-Fi network may be used to connect computers to each other, to the Internet, and to wire networks (which use IEEE 802.3-related media and functions).

Figure 16:
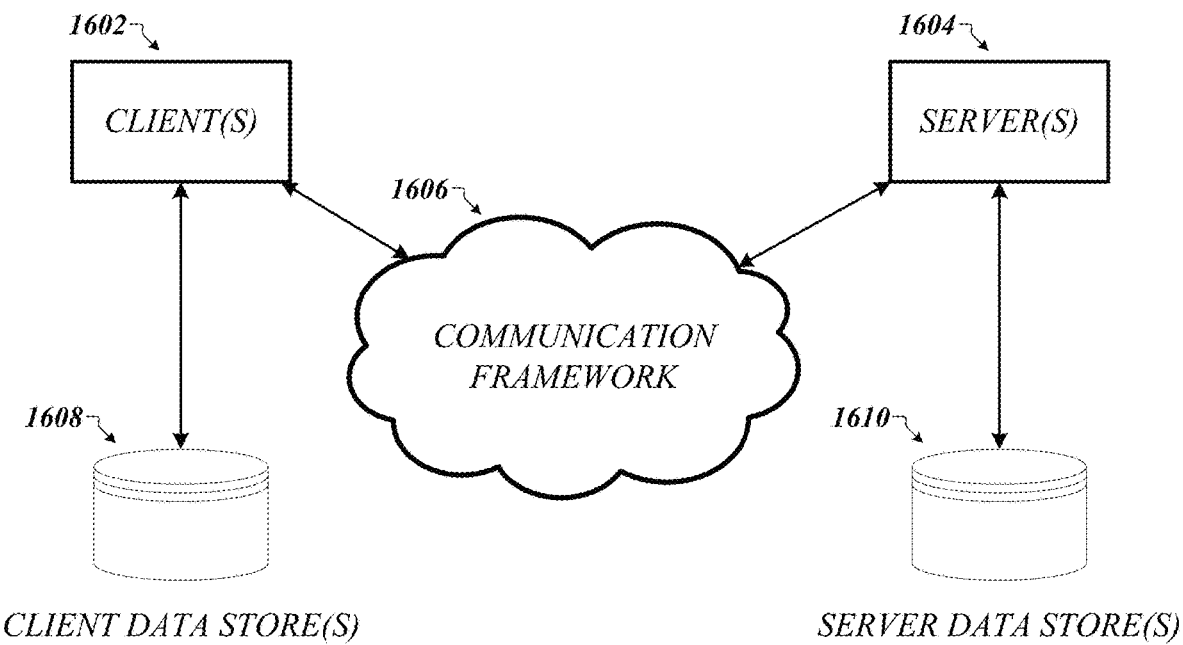
FIG. 16 illustrates an embodiment of a communications architecture according to one or more embodiments described herein.

FIG. 16 illustrates a block diagram of an exemplary communications architecture 1600 suitable for implementing various embodiments as previously described, such as virtual machine migration. The communications architecture 1600 includes various common communications elements, such as a transmitter, receiver, transceiver, radio, network interface, baseband processor, antenna, amplifiers, filters, power supplies, and so forth. The embodiments, however, may be not limited to implementation by the communications architecture 1600.

As shown in FIG. 16, the communications architecture 1600 comprises includes one or more clients 1602 and servers 1604. In some embodiments communications architecture may include one or more portions of message controller 104, message repositories, and/or laboratory data device(s)/application(s) 102. The clients 1602 and the servers 1604 may be operatively connected to one or more respective client data stores 1608 and server data stores 1610 that may be employed to store information local to the respective clients 1602 and servers 1604, such as cookies and/or associated contextual information. In various embodiments, any one of servers 1604 may implement one or more of logic flows or operations described herein, and storage medium 1400 of FIG. 14 in conjunction with storage of data received from any one of clients 1602 on any of server data stores 1610. In one or more embodiments, one or more of client data store(s) 1608 or server data store(s) 1610 may include memory accessible to one or more components of message controller 104, such as for storing online messages 108 and/or offline messages 112.

The clients 1602 and the servers 1604 may communicate information between each other using a communication framework 1606. The communications framework 1606 may implement any well-known communications techniques and protocols. The communications framework 1606 may be implemented as a packet-switched network (e.g., public networks such as the Internet, private networks such as an enterprise intranet, and so forth), a circuit-switched network (e.g., the public switched telephone network), or a combination of a packet-switched network and a circuit-switched network (with suitable gateways and translators).

The communications framework 1606 may implement various network interfaces arranged to accept, communicate, and connect to a communications network. A network interface may be regarded as a specialized form of an input output interface. Network interfaces may employ connection protocols including without limitation direct connect, Ethernet (e.g., thick, thin, twisted pair 10/100/1900 Base T, and the like), token ring, wireless network interfaces, cellular network interfaces, IEEE 802.11a-x network interfaces, IEEE 802.16 network interfaces, IEEE 802.20 network interfaces, and the like. Further, multiple network interfaces may be used to engage with various communications network types. For example, multiple network interfaces may be employed to allow for the communication over broadcast, multicast, and unicast networks. Should processing requirements dictate a greater amount speed and capacity, distributed network controller architectures may similarly be employed to pool, load balance, and otherwise increase the communicative bandwidth required by clients 1602 and the servers 1604. A communications network may be any one and the combination of wired and/or wireless networks including without limitation a direct interconnection, a secured custom connection, a private network (e.g., an enterprise intranet), a public network (e.g., the Internet), a Personal Area Network (PAN), a Local Area Network (LAN), a Metropolitan Area Network (MAN), an Operating Missions as Nodes on the Internet (OMNI), a Wide Area Network (WAN), a wireless network, a cellular network, and other communications networks.

Various embodiments may be implemented using hardware elements, software elements, or a combination of both. Examples of hardware elements may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth. Examples of software may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. Determining whether an embodiment may be implemented using hardware elements and/or software elements may vary in accordance with any number of factors, such as desired computational rate, power levels, heat tolerances, processing cycle budget, input data rates, output data rates, memory resources, data bus speeds and other design or performance constraints.

One or more aspects of at least one embodiment may be implemented by representative instructions stored on a machine-readable medium which represents various logic within the processor, which when read by a machine causes the machine to fabricate logic to perform the techniques described herein. Such representations, known as "IP cores" may be stored on a tangible, machine readable medium and supplied to various customers or manufacturing facilities to load into the fabrication machines that actually make the logic or processor. Some embodiments may be implemented, for example, using a machine-readable medium or article which may store an instruction or a set of instructions that, if executed by a machine, may cause the machine to perform a method and/or operations in accordance with the embodiments. Such a machine may include, for example, any suitable processing platform, computing platform, computing device, processing device, computing system, processing system, computer, processor, or the like, and may be implemented using any suitable combination of hardware and/or software. The machine-readable medium or article may include, for example, any suitable type of memory unit, memory device, memory article, memory medium, storage device, storage article, storage medium and/or storage unit, for example, memory, removable or non-removable media, erasable or non-erasable media, writeable or re-writeable media, digital or analog media, hard disk, floppy disk, Compact Disk Read Only Memory (CD-ROM), Compact Disk Recordable (CD-R), Compact Disk Rewriteable (CD-RW), optical disk, magnetic media, magneto-optical media, removable memory cards or disks, various types of Digital Versatile Disk (DVD), a tape, a cassette, or the like. The instructions may include any suitable type of code, such as source code, compiled code, interpreted code, executable code, static code, dynamic code, encrypted code, and the like, implemented using any suitable high-level, low-level, object-oriented, visual, compiled and/or interpreted programming language.

Certain embodiments of the present disclosure were described above. It is, however, expressly noted that the present disclosure may be not limited to those embodiments, but rather the intention may be that additions and modifications to what was expressly described herein may be also included within the scope of the disclosure. Moreover, it may be to be understood that the features of the various embodiments described herein were not mutually exclusive and may exist in various combinations and permutations, even if such combinations or permutations were not made express herein, without departing from the spirit and scope of the disclosure. In fact, variations, modifications, and other implementations of what was described herein may occur to those of ordinary skill in the art without departing from the spirit and the scope of the disclosure. As such, the disclosure may be not to be defined only by the preceding illustrative description.

The invention claimed is:

1. An apparatus, the apparatus comprising:
a processor; and
memory comprising instructions that when executed by the processor cause the processor to:
identify a set of online messages associated with a liquid chromatography or mass spectrometry procedure;
determine one or more properties for each online message in the set of online messages;
archive at least one of the online messages as an offline message based on a first set of rules and one or more properties determined for the at least one of the online messages, the at least one of the online messages archived as an offline message stored in a dump file or an external table;

generate at least one immediate attention message based on a second set of rules and a respective one or more properties for a respective online message in the set of online messages; and update an audit trail with the one or more properties for at least one of the set of online messages.

2. The apparatus of claim 1, the memory comprising instructions that when executed by the processor cause the processor to determine one or more of the first set of rules or the second set of rules based on user input via a graphical user interface (GUI).

3. The apparatus of claim 1, the memory comprising instructions that when executed by the processor cause the processor to generate a message tracking table comprising one or more characteristics for the at least one online message archived in the external table as the offline message.

4. The apparatus of claim 1, the memory comprising instructions that when executed by the processor cause the processor to retrieve the at least one online message archived in the external table based on the one or more characteristics for the at least one online message archived in the external table as the offline message.

5. The apparatus of claim 1, the memory comprising instructions that when executed by the processor cause the processor to receive the set of online messages from one or more laboratory data devices or applications.

6. The apparatus of claim 3, the one or more laboratory data devices or applications utilized in conjunction with liquid chromatography or mass spectrometry.

7. The apparatus of claim 1, the memory comprising instructions that when executed by the processor cause the processor to generate a single table with at least one of the set of online messages and the offline message archived in the external table.

8. The apparatus of claim 1, the at least one immediate attention messages comprising an email, a text message, or a phone call.

9. At least one non-transitory computer-readable medium comprising a set of instructions that, in response to being executed by a processor circuit, cause the processor circuit to:

identify a set of online messages associated with a liquid chromatography or mass spectrometry procedure;

determine one or more properties for each online message in the set of online messages;

archive at least one of the online messages as an offline message based on a first set of rules and one or more properties determined for the at least one of the online messages, the at least one of the online messages archived as an offline message stored in a dump file or an external table;

generate at least one immediate attention message based on a second set of rules and a respective one or more properties for a respective online message in the set of online messages; and update an audit trail with the one or more properties for at least one of the set of online messages.

10. The at least one non-transitory computer-readable medium of claim 9, comprising instructions that, in response to being executed by the processor circuit, cause the processor circuit to determine one or more of the first set of rules or the second set of rules based on user input via a graphical user interface (GUI).

11. The at least one non-transitory computer-readable medium of claim 9, comprising instructions that, in response to being executed by the processor circuit, cause the processor circuit to generate a message tracking table comprising one or more characteristics for the at least one online message archived in the external table as the offline message.

12. The at least one non-transitory computer-readable medium of claim 9, comprising instructions that, in response to being executed by the processor circuit, cause the processor circuit to retrieve the at least one online message archived in the external table based on the one or more characteristics for the at least one online message archived in the external table as the offline message.

13. A computer-implemented method, comprising:

identifying a set of online messages associated with a liquid chromatography or mass spectrometry procedure;

determining one or more properties for each online message in the set of online messages;

archiving at least one of the online messages as an offline message based on a first set of rules and one or more properties determined for the at least one of the online messages, the at least one of the online messages archived as an offline message stored in a dump file or an external table;

generating at least one immediate attention message based on a second set of rules and a respective one or more properties for a respective online message in the set of online messages; and update an audit trail with the one or more properties for at least one of the set of online messages.

14. The computer-implemented method of claim 13, comprising generating a message tracking table comprising one or more characteristics for the at least one online message archived in the external table as the offline message.

15. The computer-implemented method of claim 13, comprising receiving the set of online messages from one or more laboratory data devices or applications.

16. The computer-implemented method of claim 13, comprising generating a single table with at least one of the set of online messages and the offline message archived in the external table.

* * * * *